United States Patent
Sheehan et al.

(10) Patent No.: US 6,270,487 B1
(45) Date of Patent: Aug. 7, 2001

(54) ABSORBENT ARTICLES HAVING A SKIN CARE COMPOSITION DISPOSED THEREON THAT ARE AT LEAST PARTIALLY ASSEMBLED USING AN OIL RESISTANT ADHESIVE

(75) Inventors: Astrid Annette Sheehan, Cincinnati; Ted Lee Blaney, West Chester; Robert Merle Hubbard, Mason; Ramon Andres Urteaga, Forest Park, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/301,109

(22) Filed: Apr. 28, 1999

Related U.S. Application Data

(60) Provisional application No. 60/083,913, filed on May 1, 1998.

(51) Int. Cl.⁷ .................................................. A61F 13/15
(52) U.S. Cl. .............................. 604/385.28; 604/385.01; 604/385.25; 604/389
(58) Field of Search .................... 604/363, 367, 604/385.01, 385.06, 385.21, 385.23, 385.24, 385.25, 385.27, 385.28

(56) References Cited

U.S. PATENT DOCUMENTS

| | | |
|---|---|---|
| 4,824,889 | 4/1989 | Mostert . |
| 4,826,909 | 5/1989 | Lakshmanan et al. ............. 524/478 |
| 4,937,138 | 6/1990 | Mostert ............................... 428/286 |
| 4,956,207 | 9/1990 | Kauffman et al. .................. 428/34.2 |
| 5,032,120 | 7/1991 | Freeland et al. . |
| 5,455,111 | 10/1995 | Velasquez Urey ................ 428/315.6 |
| 5,536,563 | 7/1996 | Shah et al. . |
| 5,607,760 | 3/1997 | Roe ....................................... 442/375 |
| 5,853,864 | 12/1998 | Bunnelle ............................. 428/261 |
| 5,922,805 | 7/1999 | Bouttefort et al. ................ 524/590 |
| 5,948,709 | 9/1999 | Paul et al. ........................... 442/327 |
| 5,955,533 | 9/1999 | Miskovic et al. .................. 524/590 |
| 6,008,148 | 12/1999 | Harris et al. ........................ 442/381 |
| 6,010,972 | 1/2000 | Zacharias et al. .................. 442/398 |
| 6,114,261 | 9/2000 | Strelow et al. ..................... 442/153 |
| 6,166,285 | 12/2000 | Schulte et al. ..................... 604/364 |

FOREIGN PATENT DOCUMENTS

| | | |
|---|---|---|
| 0966977 | 12/1999 | (EP) . |
| 0966978 | 12/1999 | (EP) . |
| 0970710 | 1/2000 | (EP) . |
| WO 94/01507 | 1/1994 | (WO) . |
| WO 96/38739 | 10/1997 | (WO) . |
| WO 97/39075 | 10/1997 | (WO) . |
| WO 98/24391 | 6/1998 | (WO) . |
| WO 99/56796 | 11/1999 | (WO) . |

OTHER PUBLICATIONS

U.S. application No. 08/816,106, Curro et al., filed Mar. 14, 1997.
U.S. application No. 09/526,271, Blaney et al., filed Mar. 15, 2000.

*Primary Examiner*—John G. Weiss
*Assistant Examiner*—Jamisue Webb
(74) *Attorney, Agent, or Firm*—Edward Milbrada; Julia A. Glazer; Tara M. Rosnell

(57) ABSTRACT

An absorbent article, such as a diaper, containing cuffs with a skin care composition disposed thereon. The skin care composition disposed on the cuffs is transferable to the wearers skin by normal contact and/or wearer motion and/or body heat. The cuffs are at least partially assembled using an oil resistant adhesive that is both material friendly and process friendly.

15 Claims, 6 Drawing Sheets

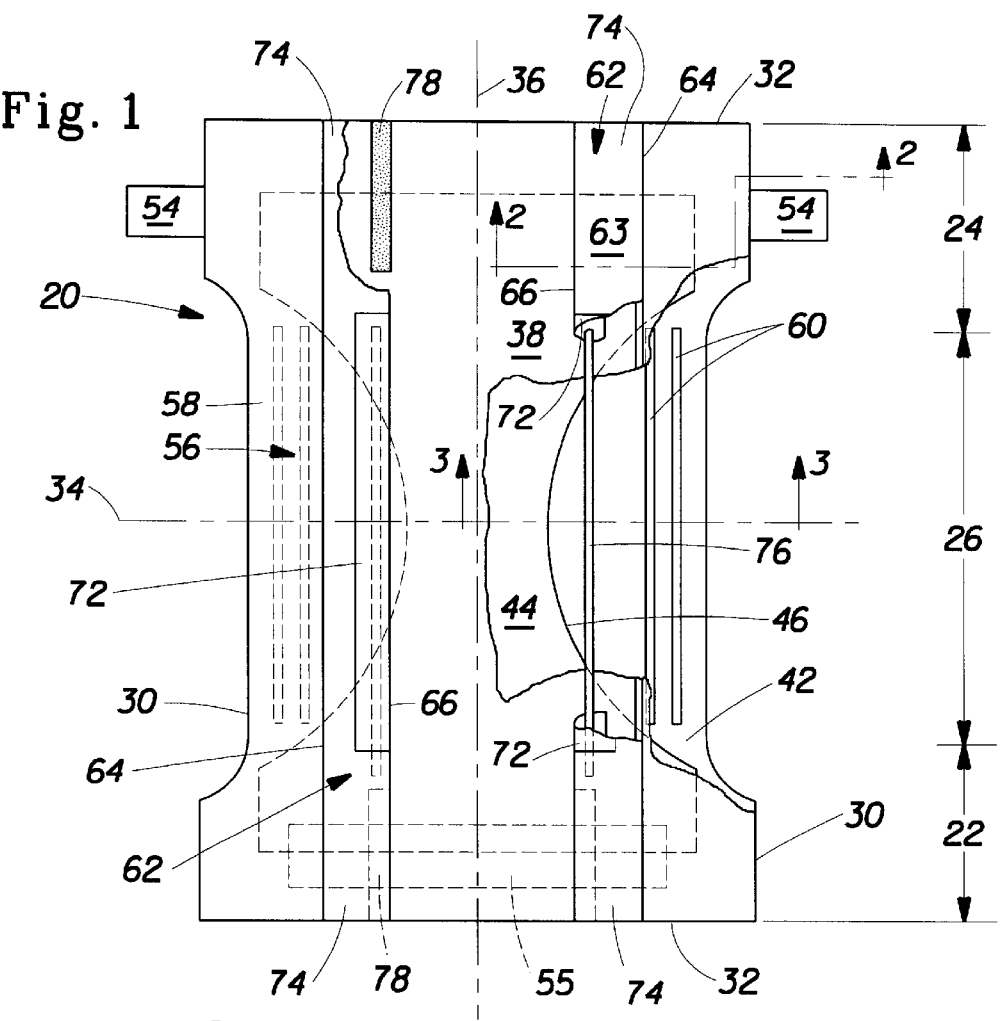
Fig. 1
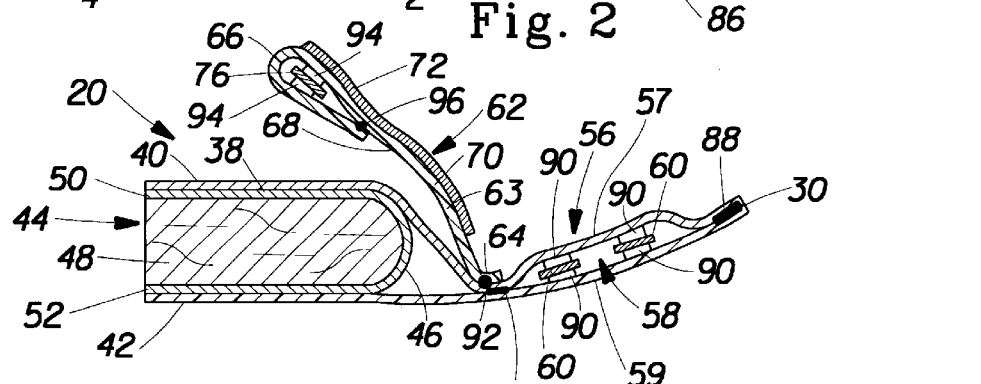
Fig. 2
Fig. 3

ABSORBENT ARTICLES HAVING A SKIN CARE COMPOSITION DISPOSED THEREON THAT ARE AT LEAST PARTIALLY ASSEMBLED USING AN OIL RESISTANT ADHESIVE

This Application claims benefit of Prov. No. 60/083,913 filed May 1, 1998.

TECHNICAL FIELD

The present invention relates to absorbent articles such as diapers, training pants, adult incontinence devices, sanitary napkins, feminine garments, and the like, having cuffs, including elastic leg cuffs. More particularly, the present invention relates to absorbent articles having a skin care composition disposed on the cuffs or the cuffs and the topsheet that is transferable to the wearer's skin by normal contact and/or wearer motion and/or body heat and means for assembling such absorbent articles that are resistant to oleaginous components of the skin care composition.

BACKGROUND OF THE INVENTION

The major function of absorbent articles such as disposable diapers and incontinent briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's legs or waist to adjacent clothing because they are not immediately absorbed within the article and the absorbent article is not able to sustain a good fit on the wearer such that gaps are created allowing the exudates to leak out of the article. For example, urine tends to be deposited onto the topsheet in gushes such that the urine migrates to the gaps between the article and the wearer where it can come in contact with clothing or other articles and be absorbed by these articles. Additionally, loose fecal material that is not easily absorbed by the absorbent article tends to "float" on the body-contacting surface and work its way past the gaps between the article and the legs or waist of the wearer.

Contemporary disposable diapers have a topsheet, a backsheet, an absorbent core, and one or more cuffs, typically elastic cuffs, positioned to contact the legs and/or waist of the wearer. These elastic cuffs prove effective generally to prevent wicking and overflow from the fluid laden diaper to clothing contacting the edges of the diaper in that the elastic cuffs present a barrier between the edge of the diaper and the contacting clothing, and generally in addition, provide a gasketing action about the legs or waist of the wearer to maintain a seal about the leg or waist and minimize gapping. However, because the forces generated by the elastic members are concentrated along a narrow area resulting in high localized pressures, such elastic cuffs have an increased tendency to indent and mark the skin of the wearer. These skin effects are particularly acute for products worn by infants and incontinent elderly adults due to the tenderness of their skin and its sensitivity to even slight pressures or rubbing actions. These skin effects are even further accentuated due to the occlusion of the skin caused by such products. The occlusion of the skin by the diaper can potentially lead to skin overhydration. As a result, overhydrated skin is more susceptible to damage from abrasion due to rubbing caused by normal wearer movements and contact with the elastic cuffs. It is also generally known that overhydrated skin is more susceptible to skin disorders, including diaper rash, erythema, heat rash, abrasion, pressure marks, and skin barrier loss. The reduced barrier efficiency of abraded, overhydrated skin can further cause an increase in diaper rash. (21 CFR § 333.503 defines diaper rash as "[a]n inflammatory skin condition in the diaper area (perineum, buttocks, lower abdomen, and inner thighs) caused by one or more of the following factors: moisture, occlusion, chafing, continued contact with urine or feces or both, or mechanical or chemical irritation.") To address the concerns of skin disorders associated with wearing diapers and other absorbent articles, the caregiver or wearer often applies skin protective and/or therapeutic products to the buttocks, genitals, anal and/or other regions before placing the absorbent article on the wearer. This procedure usually involves the caregiver applying the skin protective product to their hands, and then wiping the same on the skin of the wearer. To eliminate the need for this wasteful, messy, time-consuming, and easily forgotten procedure, there have been attempts to prepare absorbent articles which contain a skin care substance on the article's topsheet.

The art has further responded to detrimental skin effects due to using cuffs by providing absorbent articles having cuffs with a skin care composition disposed on the cuffs to provide improved skin care benefits, particularly in skin regions in contact with the cuff during use. Such skin care compositions are transferable to the wearer's skin to provide these skin benefits. Particularly useful skin care compositions and absorbent articles with cuffs having such skin care compositions disposed thereon are described in U.S. patent application Ser. No. 08/962,310, filed in the name of Schulte, et al, on Oct. 31, 1997.

However, while such skin care compositions and absorbent articles provide substantial skin care benefits, further improvements are needed. For example it is important that the skin care composition not inhibit the functionality of the cuff in the absorbent article. However, oleaginous components of the skin care composition can diffuse from the body surface of the cuff to an interior surface where such components can come into contact with the construction adhesive used to assemble the cuff. If such contact occurs, the oleaginous components can plasticize the adhesive causing a modulus reduction therein with resulting creep due to the contractive force of the elastic members within the cuffs. Such creep can ultimately cause separation of the cuff material and the elastic member with a resulting loss of contractive force and increase in leakage around the cuff.

While the art has, until the aforementioned in U.S. patent application Ser. No. 08/962,310, failed to recognize the value of applying a skin care composition to cuffs in an absorbent article, the interaction between construction adhesives for absorbent articles and topically applied lotions and ointments has been recognized. For example, PCT application Serial No. WO 97/38739, published in the names of Zacharias, et al on Oct. 23, 1997, describes elastic composites assembled using an adhesive said to have desirable oil resistance and processing properties. Claimed are elastic composites comprising two substrates wherein the first substrate is attached to the second substrate using an adhesive which has a minimum dynamic elastic modulus both before and after exposure to a commercial baby lotion, a maximum viscosity at a first temperature, and a minimum viscosity at a second lower temperature. While elastic composites made using such adhesives may have improved resistance to oleaginous components of topically applied lotions during the relatively short exposure time an absorbent article is worn (e.g. a diaper is typically worn for about three hours), improvements are needed. For example, the temperature required to achieve an adhesive viscosity low enough for use in typical glue spray apparatus may cause the adhesive temperature to be too high for use with thermally sensitive absorbent article components (e.g. low basis weight films used for backsheets).

Thus there is a need for improved construction adhesives for absorbent articles. In particular, there is a need for adhesives that have improved resistance to oleaginous components of skin care compositions for assembly of absorbent articles that may have such skin care compositions disposed thereon and for adhesives that do not unduly limit the choice of materials that may be used as components of such absorbent articles or process flexibility when applying the adhesives in the assembly of the absorbent article. These and other needs are addressed by the invention described below.

SUMMARY OF THE INVENTION

The present invention relates to an absorbent article, such as a disposable diaper, having one or more cuffs with a skin care composition disposed on (applied or migratable to) the body surface of the cuffs. In particular the invention relates to absorbent articles, particularly the cuffs thereof, that are assembled using adhesives that are resistant to oleaginous compounds used to formulate such skin care compositions.

As used herein, the term "cuff" includes leg cuffs including barrier cuffs, gasketing cuffs, combinations and variations thereof; transverse barriers and pockets/spacers; side panels; as well as waist cuffs including waist flaps, waistbands, waistcaps, and unitary waistcap/waistbands; and combinations of all or some of these cuffs.

BRIEF DESCRIPTION OF THE DRAWINGS

FIG. 1 is a plan view of a disposable diaper embodiment of the present invention having portions cut away to reveal underlying structure.

FIG. 2 is a fragmentary sectional view taken along section line 2—2 of FIG. 1.

FIG. 3 is a fragmentary sectional view taken along section line 3—3 of FIG. 1.

DETAILED DESCRIPTION OF THE INVENTION

Figure 4:
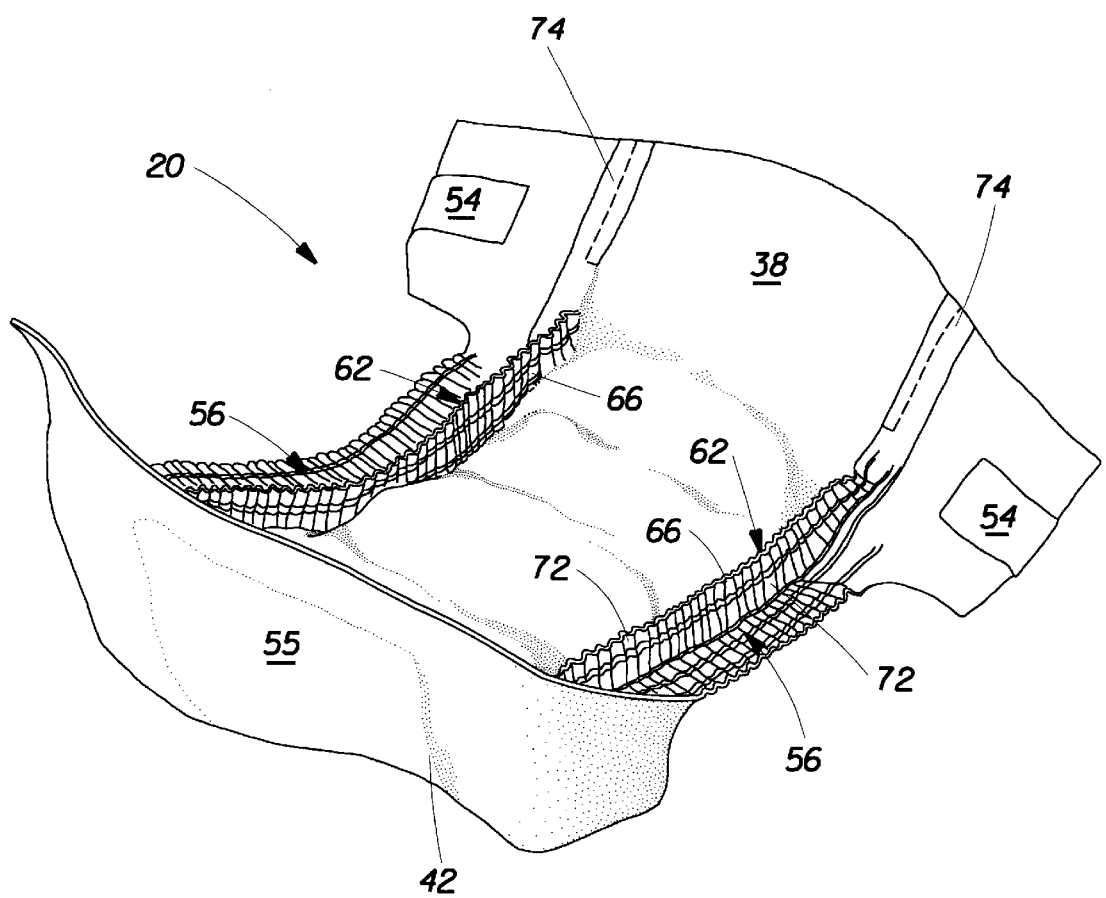
FIG. 4 is a perspective view of an absorbent article in the form of a disposable diaper according to the present invention.

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, the term "skin care composition" refers to any composition which comprises one or more agents which, when transferred from an article to a wearer's skin, provide a therapeutic and/or protective skin benefit. Representative materials are discussed in detail below.

All percentages, ratios and proportions used herein are by weight unless otherwise specified.

A. Absorbent Article

As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use. Examples of disposable absorbent articles include feminine hygiene products such as sanitary panties, sanitary napkins, and pantiliners; diapers; incontinence products such as briefs or undergarments; diaper holders; diaper inserts; pull-on diapers and training pants; and the like.

Disposable absorbent articles typically comprise a chassis comprising an outer covering layer comprising a liquid pervious topsheet and a liquid impervious backsheet joined to the topsheet, and an absorbent core encased within the outer covering layer, preferably being positioned between the topsheet and the backsheet. Disposable absorbent articles and components thereof, including the topsheet, backsheet, absorbent core, and any individual layers of these components, have two major surfaces (a first surface and a second surface) generally designated a body surface and a garment surface. As used herein, "body surface" (also referred to as the body-contacting surface or skin-contacting surface) means that surface of the article or component which is intended to be worn toward or adjacent to the body of the wearer, while the "garment surface" is on the opposite side that faces away from the wearer and is oriented toward the wearer's garments when the disposable absorbent article is worn.

The following description generally discusses the absorbent core, topsheet, and backsheet materials that are useful in disposable absorbent articles. It is to be understood that this general description applies to these components of the specific absorbent articles shown in FIGS. 1–4 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, symmetric, asymmetric, etc.). In addition to the absorbent composites of the present invention, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

The configuration and construction of the absorbent core may also be varied (e.g., the absorbent core may have varying caliper zones and/or have a profile so as to be thicker in the center; hydrophilic gradients; gradients of the absorbent composite, e.g., superabsorbent gradients; lower average density and lower average basis weight zones, e.g., acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, training pants, pantiliners, regular sanitary napkins, and overnight sanitary napkins, and to accommodate wearers ranging from infants to adults.

The absorbent core can include other absorbent components that are often used in absorbent articles, for example, a dusting layer, a wicking or acquisition layer (surge management layer), or a secondary topsheet for increasing the wearers comfort.

The topsheet is preferably compliant, soft feeling, and non-irritating to the wearer's skin. Further, the topsheet is liquid pervious, at least in certain regions, and permits liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers), bicomponent fibers, or from a combination of natural and synthetic fibers. When the topsheet comprises a nonwoven web, the web may be manufactured by a wide number of known techniques. For example, the web may be spunbonded, carded, wet-laid, melt-blown, hydroentangled, hydroformed, hydroapertured, combinations of the above, or the like.

The backsheet is preferably impervious to liquids (e.g., menses and/or urine), at least in the crotch region of the absorbent article, and is preferably manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a coated nonwoven or a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. (An example of a breathable backsheet suitable for use herein is disclosed in U.S. Pat. No. 5,571,096, issued to Dobrin, Davis and Weirich on Nov. 5, 1996, which patent is incorporated herein by reference.) The size of the backsheet is dictated by the size of the absorbent core and the exact absorbent article design selected.

The backsheet and the topsheet are positioned adjacent the garment surface and the body surface, respectively, of the absorbent core. The absorbent core is preferably joined with the topsheet, the backsheet, or both in any manner as is known by attachment members such as those well known in the art. However, embodiments of the present invention are envisioned wherein portions of the entire absorbent core are unattached to either the topsheet, the backsheet, or both.

The backsheet and/or the topsheet may be secured to the absorbent core or to each other, for example, by a uniform continuous layer of adhesive, a patterned layer of adhesive, or an array of separate lines, spirals, or spots of adhesive. Adhesives which have been found to be satisfactory for applications, such as joining topsheet or backsheet to an absorbent core where exposure to oleaginous materials is minimal, are manufactured by H. B. Fuller Company of St. Paul, Minn. under the designation HL-1358. Suitable oil resistant adhesives are discussed in detail in part C below. The attachment members will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article in which the "treated cuffs" ("treated cuffs" being used herein to designate cuffs having one or more skin care compositions disposed thereon) of the present invention may be used is a diaper. As used herein, the term "diaper" refers to an absorbent article generally worn by infants and incontinent persons that is worn about the lower torso of the wearer. In other words, the term "diaper" includes infant diapers, training pants, adult incontinence devices, and the like. The present invention is also applicable to other types of disposable products such as sanitary napkins and pantiliners that contain cuffs.

FIG. 1 is a plan view of a preferred embodiment of a diaper 20 of the present invention in its flat-out, uncontracted state (i.e., with all elastic induced contraction pulled out) with portions of the structure being cut away to more clearly show the construction of the diaper 20 and with the portion of the diaper 20 which contacts the wearer (the body surface) facing the viewer. The diaper 20 is shown in FIG. 1 to have a front waist region 22, a back waist region 24, a crotch region 26, and a periphery which is defined by the outer edges of the diaper in which the longitudinal edges are designated 30 and the end edges are designated 32. The diaper 20 additionally has a lateral centerline which is designated 34 and a longitudinal centerline which is designated 36. The diaper 20 comprises a chassis comprising (i) an outer covering layer comprising a liquid pervious topsheet 38 and a liquid impervious backsheet 42, and (ii) an absorbent core 44 having side edges 46; a fastening system preferably comprising a pair of tape-tab fasteners 54 and a landing member 55; gasketing cuffs 56 each comprising a side flap 58 and flap elastic members 60; barrier cuffs 62 comprising a barrier cuff member 63 having a proximal edge 64, a distal edge 66, and ends 74; and spacing means such as a spacing elastic member 76 for spacing the distal edge 66 away from the topsheet. The diaper 20 additionally comprises closure members 78 for securing closed the ends 74 of each barrier cuff 62. While the components of the diaper may be assembled in a variety of well known configurations, a preferred diaper configuration is described generally in U.S. Pat. No. 4,695,278 issued to Lawson on Sep. 22, 1987, and which patent is incorporated herein by reference.

FIG. 1 shows a preferred embodiment of the diaper 20 in which the topsheet 38 and the backsheet 42 are coextensive and have length and width dimensions generally larger than those of the absorbent core 44. The topsheet 38 is joined with and superposed on the backsheet 42 to thereby form the periphery of the diaper 20.

The diaper 20 has front and back waist regions 22 and 24 extending, respectively, from the end edges 32 of the periphery toward the lateral centerline 34 of the diaper 20. The waist regions comprise those portions of the diaper 20 which, when worn, encircle the waist of the wearer. The crotch region 26 is that portion of the diaper 20 between the waist regions and comprises that portion of the diaper 20 which, when worn, is positioned between the legs of the wearer and covers the lower torso of the wearer.

As shown in FIG. 1, a skin care composition 72 is disposed on each barrier cuff 62. The skin care composition 72 is preferably disposed on the body surface of the barrier cuff so that the skin care composition may readily transfer to the wearer's skin during use. In the embodiment shown, the skin care composition 72 is disposed adjacent the distal edge 66, preferably at least in the crotch region 26. More preferably, the skin care composition 72 is disposed on the distal edge 66. The barrier cuff 62 most preferably comprises one or more stripes of skin care composition 72 disposed thereon. In the embodiment shown, the skin care composition 72 is disposed on only a segment of the barrier cuff 62. For certain skin care compositions, it is preferred to avoid application of the skin care composition to the portions of the barrier cuff adjacent the ends of the spacing elastic members to insure there is no elastic creep resulting from the interaction of the skin care composition and adhesive. As is shown in FIG. 1, in a preferred embodiment the skin care composition 72 is not disposed adjacent the end of the spacing elastic member 76 in the front waist region (although it may alternatively also not be disposed adjacent the end in the back waist region). As discussed herein, the skin care composition may alternatively be applied to the garment surface of the barrier cuff and allowed to "transfer through" to the body surface so as to enhance the hydrophobicity of the barrier cuffs as well as to be disposed on the body surface so as to provide the skin care benefits. Further, the skin care composition may be applied to other portions of the barrier cuff, the entire barrier cuff, the spacing elastic members, or any other component of the barrier cuff. The skin care composition may also be disposed in any pattern, including discontinuous or continuous patterns, or in any amount as discussed hereinafter.

The diaper 20 is shown in FIG. 2 to have a garment surface 86 and a body surface 84 opposed to the garment surface 86. The body surface 84 of the diaper 20 comprises that portion of the diaper 20 which is positioned adjacent to the wearer's body during use (i.e., the body surface 84 generally is formed by at least a portion of the topsheet 38 and other components including those that may be joined to the topsheet 38). The garment surface 86 comprises that portion of the diaper 20 which is positioned away from the wearer's body during use (i.e., the garment surface 86 generally is formed by at least a portion of the backsheet 42 and other components including those that may be joined to the backsheet 42).

FIG. 2 is a fragmentary sectional view taken along line 2—2 of FIG. 1 and depicts the diaper construction in the back waist region 24 of the diaper 20. (It should be understood that the diaper construction in the front waist region 22 is substantially identical to the construction in the back waist region 24.) The absorbent core comprises an absorbent layer 48 that is shown as being completely enveloped by tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are secured together preferably by a flap attachment member 88 such as an adhesive. In a preferred embodiment, the flap elastic members do not extend into the back waist region 24 so that the gasketing cuff is not formed in this region. The barrier cuff 62 is shown as comprising a separate element, a barrier cuff member 63, secured to the topsheet 38; the proximal edge 64 being formed by securing the barrier cuff member 63 to the topsheet 38 by proximal securement member 92. The garment surface 68 of the barrier cuff 62 (also referred to as the barrier cuffs inboard surface) is secured to the body surface 40 by the closure member 78. Therefore, the distal edge 66 is closed. (i.e., it is not spaced away from the body surface 40). It should be noted that the spacing elastic member is not disposed in this region because the distal edge 66 is not designed to be spaced away from the body surface 40 in the waist regions. Therefore, the barrier cuff 62 is not open nor ready to constrain the flow of body exudates in this region. The skin care composition also is preferably not disposed on the barrier cuff in the back waist region in this particular embodiment.

FIG. 3 is a fragmentary sectional view taken along line 3—3 of FIG. 1 and depicts the diaper construction in the crotch region 26 as it is shaped before being applied to the wearer (i.e., the diaper 20 is subjected to elastic contraction). The absorbent core 44 comprises the absorbent layer 48 that is shown as being completely enveloped by the tissue layers 50 and 52. The absorbent core 44 is disposed between the topsheet 38 and the backsheet 42; both the topsheet 38 and the backsheet 42 extend beyond the side edge 46 of the absorbent core 44 to define the side flap 58. The juxtaposed areas of the topsheet 38 and the backsheet 42 are secured together preferably by a flap attachment member 88 such as an adhesive. The topsheet 38 and the backsheet 42 also enclose the flap elastic members 60 adjacent the longitudinal edge 30. The flap elastic members 60 are secured in the topsheet-backsheet formed side flap 58 preferably by elastic attachment members 90. The elastically contractible gasketing cuff 56 is thereby formed by the side flap 58 and the flap elastic members 60. The gasketing cuff has a body surface 57 oriented toward the skin of the wearer when the diaper is worn, and a garment surface 59 opposed to the body surface 57. The barrier cuff 62 is shown as being formed by securing a separate element, barrier cuff member 63, to the topsheet 38 preferably between the flap elastic members 60 and the side edge 46 of the absorbent core 44. The proximal edge 64 of the barrier cuff 62 is formed by securing the barrier cuff member 63 to the topsheet 38 by the proximal securement member 92. The spacing elastic member 76 is enclosed in a tunnel that is formed when an end of the barrier cuff member 63 is folded back upon itself; the spacing elastic member 76 being secured in the tunnel by spacing elastic attachment members 94. The distal edge 66 of the barrier cuff is spaced away from the body surface 40 by the elastic gathering action of the spacing elastic member 76. The barrier cuff 62 is shown as being ready to restrain, contain and hold body exudates until the diaper 20 is removed from the wearer. The skin care composition 72 is shown in FIG. 3 as being disposed on the body surface 70 of the barrier cuff 62 (the barrier cuff element 63) so that the skin care composition 72 may be transferred to the skin of the wearer during use.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No. 5,580,411 issued to Nease, et al. on Dec. 3, 1996; U.S. Pat. No. 5,569,232 issued to Roe, et al. on Oct. 29, 1996; and U.S. Pat. No. 5,569,234 issued to Buell, et al. on Oct. 29, 1996. Each of these patents is incorporated herein by reference.

The chassis of the diaper is shown in the drawings as comprising the main body portion (containment assembly) of the diaper. The chassis comprises at least an absorbent core and preferably an outer covering layer comprising the topsheet and the backsheet. When the absorbent article comprises a separate holder and a liner, the chassis generally comprises the holder and the liner (i.e., the chassis comprises one or more layers of material to define the holder while the liner comprises an absorbent composite such as a topsheet, a backsheet, and an absorbent core.) For unitary absorbent articles, the chassis comprises the main structure of the diaper with other features added to form the composite diaper structure; thus, the chassis for the diaper comprises the topsheet, the backsheet, and the absorbent core.

A topsheet 38 which is particularly suitable for use in the diaper 20, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8. An alternative preferred topsheet is a spunbonded nonwoven web of 22 grams per square meter basis weight as is available from Fiberweb North America, Inc. of Simpsonville, S.C., under the designation 9694.

The topsheet 38 of diaper 20 is preferably made of a hydrophilic material to promote rapid transfer of liquids (e.g., urine) through the topsheet. If the topsheet is made of a hydrophobic material, preferably at least the body surface of the topsheet, or a portion thereof, is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 issued to Reising, et al on Jan. 29, 1991 and U.S. Pat. No. 4,988,345 issued to Reising on Jan. 29, 1991, each of which is incorporated herein by reference.

In a particularly preferred embodiment as described herein, the topsheet of the absorbent article will also have a skin care composition disposed thereon. Representative treated topsheets are described in U.S. Pat. No. 5,643,588, issued to Roe, Bakes, and Warner on Jul. 1, 1997; and U.S. Pat. No. 5,635,191, issued to Roe and Mackey on Jun. 3, 1997; each of which are incorporated herein by reference. Methods for delivering a skin care composition via the repeated use of absorbent articles having such treated topsheets are disclosed in U.S. patent application Ser. No. 08/926,532, Elder, et al., filed on Sep. 10, 1997; U.S. patent application Ser. No. 08/926,926,533, Van Rijswijck, et al. filed on Sep. 10, 1997; and U.S. patent application Ser. No. 08/908,852, Roe, et al. filed on Aug. 8, 1997; each of which is incorporated herein by reference. As discussed herein, a skin care composition disposed on both the cuffs and the topsheet will facilitate transfer of the skin care composition to a greater amount of skin, in terms of surface area, relative to treatment of the cuffs only. Furthermore, application to both components may allow delivery of greater amounts of skin care composition to a given region of the wearer and/or delivery of different formulation skin care compositions for different skin benefits.

In a preferred embodiment of a diaper as described herein, the backsheet 42 has a modified hourglass shape extending beyond the absorbent core around the entire diaper periphery. The backsheet is preferably a soft, cloth-like web laminate comprising a selectively apertured polymeric formed film and a nonwoven web. Such a breathable backsheet is more fully described in U.S. Pat. No. 5,571,096 issued to Dobrin, et al. on Nov. 5, 1996, which patent is incorporated herein by reference.

The absorbent core 44 may take on any size or shape that is compatible with the diaper 20. One preferred embodiment of the diaper 20 has an asymmetric, modified T-shaped absorbent core 44 having ears in the first waist region but a generally rectangular shape in the second waist region. Exemplary absorbent structures for use as the absorbent core of the present invention that have achieved wide acceptance and commercial success are described in U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,888,231 issued to Angstadt on Dec. 19, 1989; EP Patent Application 640 330, The Procter & Gamble Company, published Mar. 1, 1995; and U.S. Pat. No. 4,834,735, issued to Alemany et al. on May 30, 1989. The absorbent core may further comprise a dual core system containing an acquisition/distribution core of chemically stiffened fibers positioned over an absorbent storage core as detailed in U.S. Pat. No. 5,234,423, issued to Alemany et al., on Aug. 10, 1993; and in U.S. Pat. No. 5,147,345, issued to Young, LaVon and Taylor on Sep. 15, 1992. All of these patents are incorporated herein by reference.

In a preferred embodiment, the diaper 20 comprises cuffs each comprising a leg cuff comprising a barrier cuff 62 and/or a gasketing cuff 56 for providing improved containment of liquids and other body exudates. The cuffs provide for improved containment of liquids and other body exudates and can be constructed in a number of different configurations. The diaper 20 may also comprise cuffs comprising an elastic waist feature (not shown) and/or elastic side panels (not shown) to provide a more contouring fit and more effective application of the diaper 20. Such cuffs may also be treated with a skin care composition.

Each leg cuff may comprise several different embodiments for reducing the leakage of body exudates in the leg regions. (The leg cuff can be and is sometimes also referred to as leg bands, side flaps, barrier cuffs, elastic leg cuffs, gasketing cuffs, or elastic cuffs.) U.S. Pat. No. 3,860,003, incorporated herein by reference, describes a disposable diaper which provides a contractible leg opening having a side flap and one or more elastic members to provide an elastic leg cuff (gasketing cuff). U.S. Pat. No. 4,909,803 issued to Aziz et al. on Mar. 20, 1990, and incorporated herein by reference, describes a disposable diaper having "stand-up" elasticized flaps (barrier cuffs) to improve the containment of the leg regions. U.S. Pat. No. 4,695,278, issued to Lawson on Sep. 22, 1987, and incorporated herein by reference, describes a disposable diaper having dual cuffs including a gasketing cuff and a barrier cuff. While each leg cuff may be configured so as to be similar to any of the leg bands, side flaps, barrier cuffs, or elastic cuffs described above, it is preferred that each leg cuff comprise barrier cuffs 62 and gasketing cuffs 56 as described in detail below.

Each barrier cuff 62 is a flexible member having a proximal edge 64, a distal edge 66, a garment surface 68 (also referred to as the inboard surface) and a body surface 70 (also referred to as the outboard surface). The garment surface 68 is oriented toward the interior of the diaper, and the body surface 70 is oriented toward the skin of the wearer when the diaper is being worn. The barrier cuff 62 may be manufactured from a wide variety of materials such as polypropylene, polyester, rayon, nylon, foams, nonwovens, plastic films, formed films, and elastic films or foams. A number of manufacturing techniques may be used to manufacture the barrier cuff. For example, the barrier cuff 62 may be woven, non-woven, spunbonded, spunbonded-meltblown-spunbonded, carded, coated, laminated or the like. A preferred barrier cuff 62 comprises a polypropylene material containing no finish or surfactant to render it liquid impermeable. An exemplary polypropylene fiber nonwoven material is manufactured by Crown Zellerbach Company as CELESTRA. A particularly preferred nonwoven material is a carded nonwoven web as is available from PGI of Landisville, N.J. under the designation 67700. Alternatively, the material may be a nonwoven web supplied by Corovin GmbH of Peine, Germany under the designation MD300A. In addition, because of the hydrophobic skin care compositions used in the present invention, the barrier cuff may be made from hydrophilic material and have a hydrophobic skin care composition disposed thereon to enhance its barrier properties.

As shown in FIGS. 1 and 3, the barrier cuff 62, and more particularly the proximal edge 64, is disposed inboard of the longitudinal edge 30, adjacent to and preferably inboard of the gasketing cuff 56. The term "inboard" is defined as the direction toward the centerline (34 or 36, respectively) of the diaper that is parallel to the respective edge of the diaper along which the particular gasketing cuff is disposed. The barrier cuff 62 is disposed adjacent the gasketing cuff 56 to provide a more effective dual restraint against the flow of body exudates. The barrier cuff 62 is preferably disposed inboard of the gasketing cuff 56 so that exudates, especially loose fecal material which is not easily absorbed and tends to float along the body surface 40, will contact the barrier cuff 62 before it can contact the gasketing cuff 56. The barrier cuff 62 is more preferably disposed between the flap elastic member 60 of the gasketing cuff 56 and the longitudinal centerline 36 of the diaper 20. Most preferably, the barrier cuff 62 is disposed between the flap elastic member 60 and the side edge 46 of the absorbent core 44 in the crotch region 26 of the diaper 20.

The proximal edge 64 and the distal edge 66 are in spaced relation to each other and define the width of the barrier cuff 62. The proximal and distal edges 64 and 66, respectively, may be in a parallel, non parallel, rectilinear or curvilinear relationship. In addition, the barrier cuff 62 may have a variety of different cross sectional areas including circular, square, rectangular or any other shape such as shown in FIG. 3. Preferably, the proximal edge 64 is spaced from the distal edge 66 in a parallel and rectilinear relationship to provide a barrier cuff 62 having uniform widths.

A preferred embodiment of the diaper 20 shown in FIGS. 2 and 3 is provided with the barrier cuff 62 joined to the topsheet 38. The term "joined" includes any means for affixing the barrier cuff 62 to the diaper 20, and includes embodiments wherein the barrier cuff 62 is a separate element having the proximal edge 64 directly or indirectly attached to the topsheet 38 (i.e., integral) or embodiments wherein the barrier cuff 62 is made from the same element or material as the topsheet 38 so that the proximal edge 64 is a continuous and undivided element of the topsheet (i.e., unitary). The barrier cuff 62 may alternatively be joined to the side flap 58, the backsheet 42, the absorbent core 44, the topsheet 38 or any combination of these or other elements of the diaper 20. In a preferred diaper 20, the barrier cuffs 62 are integral with the topsheet 38. The integral barrier cuff 62 is preferably formed by a strip of material, barrier cuff member 63, which is secured to the topsheet by proximal securement member 92, the distal edge 66 being formed by folding an end of the barrier cuff member 63 back upon itself.

The distal edge 66 is preferably disposed inboard of the proximal edge 64 to present a more effective barrier against the flow of exudates. The distal edges 66 are maintained inboard of the proximal edges 64 by the closure members 78 so as to obviate their inversion. While the distal edges 66 may alternatively be disposed in other positions in relation to the proximal edges 64, such positions are not preferred.

The distal edge 66 is preferably not secured to any other element in at least the crotch region 26 of the diaper 20 so that it may be spaced away from the body surface 40 of the topsheet 38. The distal edge 66 is preferably spaced away from the body surface 40 to enhance the containment of the article. As used herein, "spaced" includes embodiments wherein the distal edges 66 may assume one or more positions relative to the body surface 40 of the topsheet 38 including at some times assuming a position adjacent the body surface 40 of the topsheet 38. The distance between the distal edge 66 to the body surface 40 of the topsheet 38 is measured along a line drawn from the distal edge 66 to the closest part of the topsheet 38 when the distal edge 66 is positioned so as to be spaced away from the topsheet as far as possible. (i.e., in the elastically contracted position).

In addition to barrier cuffs, the leg cuffs of the present invention preferably further comprise gasketing cuffs 56. The gasketing cuffs 56 are disposed adjacent the periphery of the diaper 20, preferably along each longitudinal edge 30 so that the gasketing cuffs 56 tend to draw and hold the diaper 20 against the legs of the wearer. While the gasketing cuffs 56 may comprise any of several means as are well known in the diaper art, a particularly preferred gasketing cuff construction comprises a flexible side flap 58 and flap elastic members 60, as is described in detail in U.S. Pat. No. 3,860,003, issued to Buell on Jan. 14, 1975 and incorporated herein by reference. In addition, a method and apparatus suitable for manufacturing a disposable diaper having elastic gasketing cuffs 56 are described in U.S. Pat. No. No. 4,081,301 which issued to Buell on Mar. 28, 1978 and which patent is incorporated herein by reference.

The side flap 58 should be highly flexible and thus contractible so that the flap elastic members 60 may gather the side flap 58 to provide a gasketing cuff 56 about the legs or waist of the wearer. The side flaps 58 are preferably that portion of the diaper 20 between the periphery and the edges of the absorbent core 44. Thus, in a preferred embodiment of the present invention as shown in FIG. 1, the side flaps 58 are formed from the extension of the backsheet 42 and the topsheet 38 from and along the side edges 46 of the absorbent core 44 of the diaper 20 in at least the crotch region 26. Alternatively, as described in U.S. Pat. No. 3,860,003, the side flap may be a separate member joined to the chassis (topsheet, backsheet, and/or absorbent core) or one of the components of the side flap may be a separate member.

The flap elastic members 60 are preferably operatively joined (secured) to the side flaps 58 in an elastically contractible condition so that in a normally unrestrained configuration, the flap elastic members 60 effectively contract or gather the side flaps 58. The flap elastic members 60 can be secured to the side flaps 58 in an elastically contractible condition in at least two ways. For example, the flap elastic members 60 may be stretched and secured to the side flaps 58 while the side flaps 58 are in an uncontracted condition. Alternatively, the side flaps 58 may be contracted, for example by pleating, and the flap elastic members 60 secured to the contracted side flaps 58 while the flap elastic members 60 are in their unrelaxed or unstretched condition. The gasketing cuffs may alternatively comprise a number of different elastically extensible structures such as elastic nonwoven webs or foams; stretch laminates such as is described in U.S. Pat. No. 5,151,092 issued to Buell, et al. on Sep. 29, 1992, incorporated herein by reference; and structural elastic-like film (SELF) webs such as are described in U.S. Pat. No. 5,518,801 issued to Chappell, et al. on May 21, 1996, and incorporated herein by reference.

In the embodiment illustrated in FIG. 1, the flap elastic members 60 extend essentially the entire length of the side flaps 58 in the crotch region 26 of the diaper 20. Alternatively, the elastic members 60 may extend the entire length of diaper 20, or any other length suitable to provide a gasketing cuff. The length of the flap elastic members 60 is dictated by the diaper's design.

One flap elastic member 60 which has been found to be suitable is an elastic strand made from natural rubber as available from Easthampton Rubber Thread Company of Stewart, Va., under the trademark L-1900 Rubber Compound. Other suitable flap elastic members 60 can be made from natural rubber, such as elastic tape sold under the trademark Fulflex 9211 by Fulflex Company of Scotland, N.C. An exemplary elastic member is a Lycra strand such as is available from DuPont Co. of Waynesboro, Va. under the designation Lycra-XA T-151. The flap elastic member 60 may also comprise any heat shrinkable elastic material as is well known in the art. Other suitable flap elastic members 60 may comprise a wide variety of materials as are well known in the art including elastomeric films, Lycra films or strands, polyurethane films, elastomeric foams, and formed elastic scrim.

In addition, the flap elastic members 60 may take a multitude of configurations. For example, the width of the flap elastic members 60 may be varied from about 0.25 mm (0.01 inches) to about 25 mm (1.0 inch) or more; the flap elastic members 60 may comprise a single strand of elastic material or may comprise several parallel or non-parallel strands of elastic material; or the flap elastic members 60 may be rectilinear or curvilinear. Still further, the flap elastic members 60 may be affixed to the diaper 20 in any of several ways which are well known in the art. For example, the flap elastic members 60 may be ultrasonically bonded, heat/pressure sealed into the diaper 20 using a variety of bonding patterns, or the flap elastic members 60 may simply be glued to the diaper 20.

In the diaper 20 of FIG. 3, the flap elastic members 60 are associated with the side flaps 58 by securing them to the side flaps 58 with elastic attachment members 90. The elastic attachment members 90 should be flexible and of sufficient adhesiveness to hold the flap elastic member in its stretched condition. The elastic attachment members 90 herein are preferably glue beads or spirals made of hot melt adhesives. A more detailed description of the manner in which the flap elastic members 60 may be positioned and secured to the diaper 20 can be found in U.S. Pat. No. 4,253,461 issued to Strickland and Visscher on Mar. 3, 1981, and U.S. Pat. No. No. 4,081,301 issued to Buell on Mar. 28, 1978, both of which are incorporated herein by reference.

Similarly, the barrier cuff 62 may be formed by securing a separate element, barrier cuff member 63, to the topsheet 38 preferably between the flap elastic members 60 and the side edge 46 of the absorbent core 44. The proximal edge 64 of the barrier cuff 62 is formed by securing the barrier cuff member 63 to the topsheet 38 by the proximal securement member 92. The spacing elastic member 76 is enclosed in a tunnel that is formed when an end of the barrier cuff member 63 is folded back upon itself; the spacing elastic member 76 being secured in the tunnel by spacing elastic attachment members 94.

Oil resistant adhesive materials suitable for use as any or all of a flap attachment member 88, an elastic attachment member 90, a proximal securement member 92, or a spacing elastic attachment member 94 are discussed in detail below in Section C.

One of skill in the art will recognize that the same considerations discussed above with respect to the side flaps 58 and the barrier cuff 62 are applicable to other components of the diaper 20. Exemplary components (none shown in FIGS. 1–4) include but are not limited to: elastic waist features, elastic side panels, pockets for receiving and containing waste, spacers for providing voids for waste, ands barriers which limit the movement of waste in the article. Such components are also considered to be cuffs for the purposes of the present invention. These various components are discussed in greater detail in the aforementioned U.S. patent application Ser. No. 08/962,310, the disclosure of which is incorporated herein by reference.

Exemplary fastening systems 54 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. No. 3,848,594, issued to Buell on Nov. 19, 1974; U.S. Pat. No. 4,963,140 issued to Robertson et al. on Oct. 16, 1990; U.S. Pat. No. B1 4,662,875, issued to Hirotsu et al. on May 5, 1987; and U.S. Pat. No. 5,151,092, issued to Buell et al. on Sep. 29, 1992; each of which is incorporated herein by reference. A skin care composition may be disposed on one or more components of the fastening system to further enhance skin health. For example, a skin care composition as described herein may be disposed on the tape tabs to ease the effects of the tape tab chafing the skin.

FIG. 4 is a perspective view of the diaper 20 in its elastically contracted position prior to being placed on the wearer. The topsheet 38 is shown as a portion of the body surface of the diaper 20, the backsheet 42 being disposed away from the body of the wearer. The gasketing cuffs 56 are shown to be gathered or contracted by the flap elastic members (not shown in FIG. 4). The diaper 20 is shown as having two barrier cuffs 62 extending adjacent to and inboard of the gasketing cuffs 56. The distal edges 66 are shown to be gathered and contracted by the spacing elastic members (not shown) in the crotch region. In addition, the ends 74 of the barrier cuff 62 are secured closed so as to provide comfort for the wearer, to obviate inversion of the barrier cuffs, and for ease of application of the diaper. A skin care composition 72 is disposed on the body surface of (applied to the body surface or applied to be migratable to the body surface of) each barrier cuff 62 so as to transfer to the skin of the wearer so as to provide the skin benefits discussed herein.

The diaper 20 is applied to a wearer by positioning the back waist region 24 under the wearer's back, and drawing the remainder of the diaper 20 between the wearer's leg so that the front waist region 22 is positioned across the front of the person. The ends of the tape-tab fasteners 54 are then secured preferably to the landing member 55 to close the diaper 20. In this manner, the barrier cuffs 62 should be disposed in the crotch region of the wearer and should provide the dispositions and functions described hereinbefore. Once applied, the distal edges 66 of the barrier cuffs 62 extend through the groin areas and diverge upwardly along both of the buttocks of the wearer. Neither of the barrier cuffs 62 encircle the thighs of the wearer. However, the gasketing cuffs 56 will encircle the thighs and create a gasketing action against the thighs. The barrier cuffs 62 contact the skin of the wearer and transfer the skin care composition 72 thereto to provide some or all of the benefits described herein.

The treated cuffs of the present invention are also useful in training pants or pull-on diapers. The term "training pants", as used herein, refers to disposable garments having fixed sides thereby defining a fixed waist opening and leg openings. Training pants are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993; U.S. Pat. No. 4,940,464 issued to Van Gompel, et al. on Jul. 10, 1990; and U.S. Pat. No. 5,092,861 issued to Nomura, et al. on Mar. 3, 1992 each of which is incorporated herein by reference. The treated cuffs of the present invention are also applicable to absorbent articles that are a combination or "hybrid" of training pants and diapers (pull-on diapers) as are described in U.S. Pat. No. 5,569,234, issued to Buell and Carlin on Oct. 29, 1996 incorporated herein by reference.

Another disposable absorbent article for which the treated cuffs of the present invention are useful are incontinence articles. The term "incontinence article" refers to pads, undergarments (pads held in place by a suspension system of some type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and PCT Publication No. WO 92/11830, The Procter & Gamble Company, published on Jul. 23, 1992; each of which is incorporated herein by reference.

Another disposable absorbent article of the present invention are feminine hygiene articles, such as sanitary napkins. Suitable feminine hygiene articles are disclosed in U.S. Pat. No. 4,556,146, issued to Swanson et al. on Dec. 3, 1985; U.S. Pat. No. B1 4,589,876, issued to Van Tilburg on Apr. 27, 1993; U.S. Pat. No. 4,687,478, issued to Van Tilburg on Aug. 18, 1997; U.S. Pat. No. 4,950,264, issued to Osborn, III on Aug. 21, 1990; U.S. Pat. No. 5,009,653, issued to Osborn, III on Apr. 23, 1991; U.S. Pat. No. 5,267,992, issued to Van Tilburg on Dec. 7, 1993; U.S. Pat. No. 5,389,094, issued to Lavash et al. on Feb. 14, 1995; U.S. Pat. No. 5,413,568, issued to Road et al. on May 9, 1995; U.S. Pat. No. 5,460,623, issued to Emenaker et al. on Oct. 24, 1995; U.S. Pat. No. 5,489,283, issued to Van Tilburg on Feb. 6, 1996; U.S. Pat. No. 5,569,231, issued to Emenaker et al. on Oct. 29, 1996; and U.S. Pat. No. 5,620,430, issued to Bamber on Apr. 15, 1997; each of which is incorporated herein by reference.

B. Skin Care Composition

While the specific skin care composition(s) delivered (referred to herein as "skin care composition" and "composition") in accordance with the present invention is an important factor in delivering desirable skin effects, it is preferred that the skin care composition should provide a protective, nonocclusive function (e.g., a relatively liquid impervious but vapor pervious barrier) to avoid skin hyperhydration and skin exposure to materials contained in body exudates; an abrasion minimizing function to reduce skin irritation in the areas where the cuffs contact the wearer's skin; or contain agents that deliver, either directly or indirectly, skin care benefits. For example, indirect benefits include improved removal of skin irritants such as feces or urine. The composition may be in a variety of forms, including, but not limited to, emulsions, lotions, creams, ointments, salves, powders, suspensions, encapsulations, gels, and the like.

As used herein, the term "effective amount of a skin care composition" refers to an amount of a particular composition which, when applied or migrated to ("disposed on") the body surface of a cuff, will be effective in reducing the abrasion between the cuff and skin in the areas where the cuffs contact the wearer's skin, providing a protective barrier and/or delivering a skin care benefit when delivered via cuffs, and/or reducing the adherence of BM to the skin. Unless otherwise indicated, the description pertaining to disposition of skin care composition on the cuffs will be applicable to compositions disposed on the topsheet, in such preferred embodiments. Of course, the effective amount of composition disposed on the cuff will depend, to a large extent, on the particular skin care composition used. Nonetheless, the quantity of the skin care composition disposed on at least a portion of the body surface of the cuff will preferably range from about 0.05 mg/in$^2$ (0.0078 mg/cm$^2$) to about 80 mg/in$^2$ (12 mg/cm$^2$), more preferably from about 1 mg/in$^2$ (0.16 mg/cm$^2$) to about 40 mg/in$^2$ (6 mg/cm$^2$), still more preferably from about 4 mg/in$^2$ (0.6 mg/cm$^2$) to about 26 mg/in$^2$ (4 mg/cm$^2$). These ranges are by way of illustration only and the skilled artisan will recognize that the nature of the composition will dictate the level that must be disposed thereon to achieve the desired skin benefits, and that such levels are ascertainable by routine experimentation in light of the present disclosure.

While the level of skin care composition disposed on the cuffs is an important aspect of the present invention, more important is the amount of composition transferred to the wearer's skin during use of one or more of the treated cuffs. Though the requisite level delivered to the skin to provide the desired skin benefits will depend to some degree on the nature of the composition employed, Applicants have found that relatively low levels may be delivered while still providing the desired skin effects. This is particularly true for preferred compositions, such as those described in the examples.

Another benefit of the present invention is the controlled application of the skin care composition to deliver the low but effective levels of composition required. This is in contrast to typically sporadic manual application of skin care agents, where the caregiver/user often applies significantly greater levels of material than are needed. Excessive materials added manually may adversely impact the fluid handling properties of the absorbent article, as a result of transfer from the skin to the article. Indeed, for certain materials, such as petrolatum, the levels applied manually may actually result in an occlusive effect, thereby compromising the skin. A benefit of the present invention is providing a barrier to surface moisture while avoiding occlusion of the skin (i.e., maintaining skin breathability). Thus, the present invention allows transfer of optimal levels of the composition to the skin to maintain and/or improve skin health.

With regard to the level of skin care composition that is transferred to the wearer during use of one treated absorbent article worn for a period of about 3 hours (a typical daytime wear time), particularly for preferred skin care compositions such as that described in Example 1, preferred is where at least about 0.01 mg/in$^2$ (0.0016 mg/cm$^2$), more preferably at least about 0.05 mg/in$^2$ (0.0078 mg/cm$^2$), still more preferably at least about 0.1 mg/in$^2$ (0.016 mg/cm$^2$), of the composition is transferred to the skin over a three hour wear period. Typically, the amount of composition delivered by one treated article will be from about 0.01 mg/in$^2$ (0.0016 mg/cm$^2$) to about 8 mg/in$^2$ (1.24 mg/cm$^2$), more preferably from about 0.05 mg/in$^2$ (0.0078 mg/cm$^2$) to about 6 mg/in$^2$ (0.93 mg/cm$^2$), still more preferably from about 0.1 mg/in$^2$ (0.016 mg/cm$^2$) to about 5 mg/in$^2$ (0.78 mg/cm$^2$), over a three hour wear period.

It will be recognized that of the numerous materials useful in the skin care compositions delivered to skin in accordance with the present invention, those that have been deemed safe and effective skin care agents are logical materials for use herein. Such materials include Category I actives as defined by the U.S. Federal Food and Drug Administration's (FDA) Tentative Final Monograph on Skin Protectant Drug Products for Over-the-Counter Human Use (21 CFR § 347), which presently include: alantoin, aluminum hydroxide gel, calamine, cocoa butter, dimethicone, cod liver oil (in combination), glycerin, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Federal Food and Drug Administration's Tentative Final Monograph on Skin Protectant Drug Products for Over-the-Counter Human Use (21 CFR § 347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like. It will be recognized that one or more of these optional materials may be used in combination with other ingredients, such as those described herein.

As will be discussed hereinafter, the skin care compositions useful in the present invention preferably, though not necessarily, have a melting profile such that they are relatively immobile and localized on the wearer-contacting surface (body surface) of the cuff at room temperature, at least a portion of the composition will be transferable to the wearer at body temperature, and yet are not completely liquid under extreme storage conditions. Preferably, the compositions are easily transferable to the skin by way of normal contact, wearer motion, and/or body heat. Because the composition preferably is substantially immobilized on the cuffs wearer-contacting surface, relatively low levels of skin care composition are needed to impart the desired skin care benefits. In addition, special barrier or wrapping materials may be unnecessary in packaging the articles useful in the present invention.

In a preferred embodiment, the skin care compositions useful herein are solid, or more often semi-solid, at 20° C., i.e. at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes some minor liquid components.

Preferably, the compositions of the present invention have a zero shear viscosity between about $1.0 \times 10^6$ centipoise and about $1.0 \times 10^8$. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., 1.0 sec$^{-1}$) using a plate and cone viscometer (a suitable instrument is available from TA Instruments of New Castle, DE as model number CSL 100). One of skill in the art will recognize means other than high melting point components (as are discussed below) can be used to provide zero shear viscosities. Exemplary means include establishing a structure having a yield value using components such as clays or fumed silica as is known in the art. Zero shear viscosity can also measured for such compositions comprising such alternative means by extrapolating a plot of viscosity vs. shear rate to a shear rate of zero at a temperature of about 20° C.

Preferred compositions are at least semi-solid at room temperature to minimize composition migration. In addition, the compositions preferably have a final melting point (100% liquid) above potential "stressful" storage conditions that can be greater than 45° C. (e.g., warehouse in Arizona, car trunk in Florida, etc.). Specifically, preferred compositions will have the following melt profile:

TABLE 1

| Characteristic | Preferred Range | Most Preferred |
| --- | --- | --- |
| Percent liquid at room temp. (20° C.) | 2–50 | 3–25 |
| Percent liquid at body temp. (37° C.) | 25–95 | 30–90 |
| Final melting point (° C.) | $\geq 38$ | $\geq 45$ |

By being solid or semisolid at ambient temperatures, preferred compositions do not have a tendency to flow and migrate to a significant degree to undesired locations of the absorbent article. This means less skin care composition is required for imparting desirable therapeutic, protective and/or conditioning benefits.

To enhance immobility of preferred compositions, the viscosity of the formulated compositions should be as high as possible to prevent flow from the cuff to undesired locations within the diaper. Unfortunately, in some instances, higher viscosities may inhibit transfer of composition to the wearer's skin or may be difficult to apply without processing problems. Therefore, a balance should be achieved so the viscosities are high enough to keep the compositions localized on the body surface of the cuff, but not so high as to impede transfer to the wearer's skin. Suitable viscosities for the compositions will typically range from about 1 to about 5000 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For compositions designed to provide a skin care benefit, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerin and derivatives thereof, including glyceride, acetoglycerides, and ethoxylated glycerides of $C_{12}$–$C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients.

Suitable petroleum-based emollients include those hydrocarbons, or mixtures of hydrocarbons, having chain lengths of from 6 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}$–$C_{28}$ fatty acids, preferably $C_{16}$–$C_{22}$ saturated fatty acids, and short chain ($C_1$–$C_8$, preferably $C_1$–$C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}$–$C_{28}$, preferably $C_{12}$–$C_{16}$) and shorter chain fatty acids e.g., lactic acid, such as lauryl lactate and cetyl lactate.

Suitable alkyl ethoxylate type emollients include $C_{12}$–$C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}$–$C_{22}$ fatty alcohols, preferably $C_{16}$–$C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

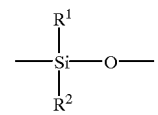

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282 (Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable humectants include glycerin, propylene glycol, sorbitol, trihydroxy stearin, and the like.

When present, the amount of emollient that can be included in the composition will depend on a variety of factors, including the particular emollient involved, the skin benefits desired, the other components in the composition and like factors. The composition will comprise from 0 to about 100%, by total weight, of the emollient. Preferably, the composition will comprise from about 10 to about 95%, more preferably from about 20 to about 80%, and most preferably from about 40 to about 75%, by weight, of the emollient.

Another optional, but especially key component of certain skin care compositions useful in the present invention is an agent capable of immobilizing the composition (including the preferred emollient and/or other skin condition/ protective agents) in the desired location in or on the treated cuff. Because certain of the preferred emollients in the composition have a plastic or liquid consistency at 20° C., they tend to flow or migrate, even when subjected to modest shear. When applied to a body surface or other location of a cuff, especially in a melted or molten state, the emollient will not remain primarily in or on the treated region. Instead, the emollient will tend to migrate and flow to undesired regions of the absorbent article.

Specifically, if the emollient migrates into the interior of the article, it can cause undesired effects on the absorbency of the absorbent core due to the hydrophobic characteristics of many of the emollients and other skin conditioning agents used in the compositions useful in the present invention. It also means that much more emollient has to be applied to the cuff to get the desired benefits. Increasing the level of emollient not only increases the cost, but also exacerbates the undesirable effect on the absorbency of the core and undesired transfer of composition during processing/ converting of the treated cuffs.

The immobilizing agent counteracts this tendency of the emollient to migrate or flow by keeping the emollient primarily localized on the surface or in the region of the cuff to which the composition is applied. This is believed to be due, in part, to the fact that the immobilizing agent raises the melting point and/or viscosity of the composition above that of the emollient. Since the immobilizing agent is preferably miscible with the emollient (or solubilized in the emollient with the aid of an appropriate emulsifier or dispersed therein), it entraps the emollient on the surface of the wearer contacting surface of the cuff or in the region to which it is applied.

It is also advantageous to "lock" the immobilizing agent on the wearer contacting surface or the region of the cuff to which it is applied. This can be accomplished by using immobilizing agents which quickly set up (i.e., solidify) upon application to the cuff. In addition, outside cooling of the treated cuff via blowers, fans, cold rolls, etc. can speed up crystallization of the immobilizing agent.

In addition to being miscible with (or solubilized in) the emollient, the immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the preferred properties of the skin care composition provide the skin benefits described herein. Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated cuff.) Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using cuffs to which the composition is applied, these esters and amides should also be relatively mild and non-irritating to the skin.

Suitable polyhydroxy fatty acid esters for use in the present invention will have the formula:

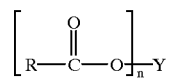

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof;

Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di-laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of: $-CH_2-(CHOH)_n-CH_2OH$, $-CH(CH_2OH)-[(CHOH)_{n-1}]-CH_2OH$, $-CH_2OH-CH_2-(CHOH)_2(CHOR^3)(CHOH)-CH_2OH$, where n is an integer from 3 to 5, and $R^3$ is H or a cyclic or aliphatic monosaccharide. Most preferred are the glycityls where n is 4, particularly $-CH_2-(CHOH)_4-CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

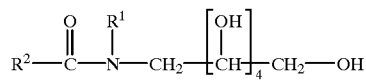

wherein $R^1$ is methyl or methoxypropyl; $R^2$ is a $C_{11}$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include Steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as carnauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the cuff. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc. of West Babylon, N.Y.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

Compositions can comprise other components typically present in emulsions, creams, ointment, lotions, powders, suspensions, etc. of this type. These components include water, viscosity modifiers, perfumes, disinfectant antibacterial actives, antiviral agents, vitamins, pharmaceutical actives, film formers, aloe vera, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzylkonnium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerin, cyclomethicone, polyethylene glycols, hexalene glycol, diol and multi-hydroxy based solvents. Suitable vitamins include A, D-3, E, B-5 and E acetate.

C. Adhesives Resistant to Oleaginous Materials

General Requirements

As discussed above, suitable materials for use in the assembly of absorbent articles according to the present invention are resistant to oleaginous components of the skin care compositions discussed herein and, at the same time, not unduly limiting to either material choice or process flexibility. For example, a suitable material for use as spacing elastic attachment member 94 must maintain the spacing elastic member 76 in a secured relationship with the barrier cuff member 63 even on exposure to oleaginous components (i.e. suitable materials are, of necessity, oil resistant). Suitable materials should also have visco-thermal properties such that: 1) the application temperature of the material is not so high as to limit the choice of other materials used to assemble the absorbent article (i.e. the adhesives are material friendly), 2) the energy required to melt the material is not so great so as to require an inordinate amount of time before the material has a suitably low viscosity for use (i. e. the time required to reach the application temperature should not be unacceptably large), and 3) the in-use properties of the melted material should be such that the material does not create application process reliability issues. Each of these criteria will be discussed in detail in the following paragraphs.

Oil Resistance

A key criterion for adhesive material suitability for use in assembling absorbent articles of the present invention, such as for use as a spacing elastic attachment member 94 in diaper 20, is resistance to the liquids to which such adhesives may be exposed during assembly, shipment, storage, or use of the absorbent article. Exemplary liquids include water, aqueous bodily exudates, such as urine, other bodily exudates, such as menses or feces, and oleaginous components of skin care compositions, such as mineral oil, petrolatum, fatty alcohols, fatty acids, silicone compounds, and other materials as may be listed in the description of the skin care composition of the present invention above.

While resistance to all the various types of liquids listed above is important, the art has had particular difficulty in providing resistance to oleaginous materials, such as the components of skin care compositions as have been found to provide desirable skin health benefits when applied to diapers. The Applicants have found that, for cuffs that have been treated with skin care compositions as are described herein, creep values less than about 0.35 inches (8.9 mm) are highly desirable. Specifically, when a sample of at least about 25 cuffs is evaluated for creep according to the method described in the TEST METHODS section below, no more than about 10 percent of the ends should have a creep value greater than about 0.35 inches (8.9 mm). Preferably, fewer than about 7.5 percent of the ends should have a creep value greater than about 0.35 inches (8.9 mm), more preferably, fewer than 5 percent of the ends.

Table 3 of Example 3 lists average creep values and percentage of fiber ends having a creep value greater about 0.35 inches (8.9 mm) for barrier cuffs 62 that have been assembled using various adhesives and treated with a skin care composition (creep data for cuffs 62 assembled using a non oil resistant prior art adhesive that were not treated with a skin care composition are also included for comparison). Examples 1 and 2 describe the assembly and treatment of diapers with such cuffs. The cuffs were then evaluated for creep resistance according to the method described in the TEST METHODS section below. As can be seen: 1) the creep resistance of the prior art non oil resistant adhesive degrades substantially when the cuff is treated with a skin care composition; and 2) the creep resistance of cuffs 62 assembled using both the prior art oil resistant adhesive and the oil resistant adhesive of the present invention in the presence of a skin care composition is substantially the same as the creep resistance of an untreated cuff assembled using the non oil resistant prior art adhesive. In other words, using oil resistant adhesives minimizes limitations on the formulation and disposition of any skin care composition that may be applied to a diaper.

Adhesive compositions comprising a butylene (1-butene) homopolymer or copolymer have been found to have particularly desirable oil resistance. Such adhesives may further comprise other polymers or copolymers, tackifying resins, waxes, stabilizers, and the like as is known to the art. Adhesive compositions of this type are also known to the art as hot melt adhesives. The Applicants believe that such oil resistance is due to the crystalline nature of polybutylene polymers. As is known, block copolymers, which are frequently components of hot melt adhesives, have regions of crystallinity and amorphous regions. The Applicants believe that such amorphous regions provide sites where oleaginous components of skin care compositions can more readily interact with polymeric components of hot melt adhesives (causing plasticization) compared to the crystalline regions. Since butylene polymers are substantially crystalline with little, if any, amorphous character, oil resistance is improved.

Material Friendliness

Another important criterion for suitability according to the present invention is "material friendliness". As used herein, an adhesive is "material friendly" if, when the adhesive is used in the assembly of an absorbent article, the use of the adhesive does not cause undue limitations on the types of materials available for use as a component of an absorbent article. For example, adhesive application temperatures of about 375° F. (191° C.) have been found to create holes in the low basis weight films that are often used as a backsheet for absorbent articles. This temperature sensitivity effectively places an upper limit on the application temperature for suitable hot melt adhesives.

The Applicants have found that the oil resistant adhesives of the present invention provide improved material friendliness. Such friendliness is shown in Example 4 which compares the behavior of an oil resistant adhesive of the present invention with an oil resistant adhesive of the prior art. As can be seen, when the adhesives of the present invention are used in combination with typical topsheet and backsheet materials in the assembly of a diaper side flap, such flaps have desirable oil resistance and improved backsheet integrity (compared to prior art oil resistant adhesives). Importantly, the changes to the backsheet when adhesives of the present invention are used are aesthetic in nature and do not substantially affect the utility of the diaper. On the other hand, the changes to the backsheet caused by the necessarily higher application temperature of the prior art oil resistant adhesives can affect diaper performance (e.g. the holes can be a source of leaks).

Process Friendliness

Materials suitable for the present invention are also process friendly. As used herein, a material is "process friendly" if it does not put unnecessary constraints on the adhesive application and use process. Specific examples of process friendly attributes include a low heat of melting to allow rapid melting of solid adhesive in a production atmosphere, low in use viscosity to minimize the pressure required to cause the adhesive to flow through application nozzles, and rapid set up on cooling to minimize unintended adhesive flow as may cause bleedthrough to process rolls. Each of these adhesive properties is discussed in greater detail below.

Rapid melting is useful because the time required to bring an adhesive to a use ready condition is one of the factors that require the attention of those operating the process. Short melt times mean that less operator attention is required after replenishing a depleted adhesive supply container.

As noted above, low viscosity at process conditions is important to minimize the pressure required to cause an adhesive to flow through application nozzles when the adhesive is used to join materials as an absorbent article is assembled. As one of skill in the art will recognize, low in use viscosity can be achieved by applying an adhesive at an elevated use temperature. However, such an approach to achieving a low in use viscosity causes additional issues. For example, it may be necessary to heat the adhesive to a temperature greater than that required for the adhesive to be material friendly. Another issue with elevated temperature is "pot life". Since hot melt adhesives are compositions comprising organic materials, the materials can begin to degrade if they are held at an elevated temperature for too long a time. "Pot life" is the time that an adhesive can be held in the melt before material properties become unacceptable (e.g. viscosity loss because of molecular weight degradation). Again, if a satisfactory viscosity can be achieved at a lower application temperature, pot life can be extended.

Process hygiene is also important in the production of absorbent articles. Adhesive set up time is important in this context because, if set up time is too long, a fluid adhesive can permeate through a material (e.g. a nonwoven cuff component) and contaminate underlying rolls. Once a roll is contaminated with an adhesive material, any webs being carried by the roll can become attached to and wrap the roll causing a break in the web.

Adhesive Material Properties

The above identified qualitative criteria for material friendliness and process friendliness help identify several material properties of importance for adhesives of the present invention. In particular:

1) The viscosity/temperature relationship (visco-thermal properties) defines the application temperature. And 2) The amount of energy required to raise the adhesive to that application temperature defines the ease of melting.

Each of these properties is discussed in detail below.

The visco-thermal properties can be defined by considering the following:

In order to be considered material friendly according to the present invention an adhesive material should have a application temperature of less than about 350° F. (177° C.). Otherwise, as noted above, visible defects begin to appear in certain useful web materials. Preferably, the application temperature is less than about 325° F. (162° C.).

Materials having an apparent viscosity of less than about 8000 centipoise will have satisfactory flow through application nozzles. Preferably, the apparent viscosity is less than about 6000 centipoise. Apparent viscosity can be measured according to ASTM Standard Method D3236-88.

The adhesive should have rapid set up to insure that permeation through porous webs is acceptably low.

Figure 6:
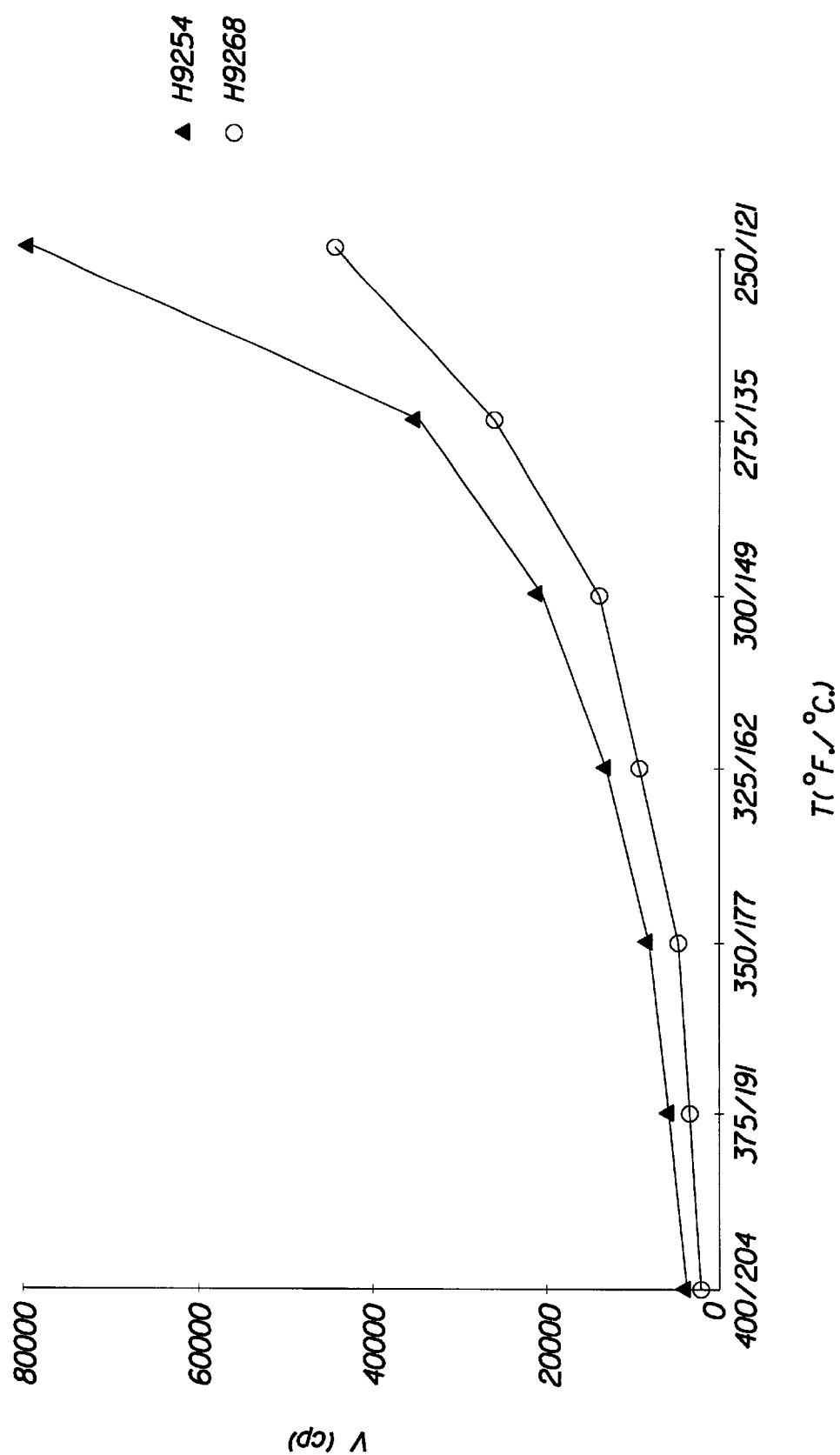
FIG. 6 is a graph comparing the apparent viscosity as a function of temperature for an oil resistant adhesive composition of the prior art and an oil resistant adhesive composition of the present invention.

FIG. 6 is a graph of apparent viscosity (V) vs. temperature (T) of a prior art oil resistant adhesive (H9254) and an oil resistant adhesive (H9268) of the present invention. As can be seen, the oil resistant adhesive of the present invention has a lower apparent viscosity than prior art oil resistant adhesive at each of the temperatures where data were taken. Such lower viscosity is most evident at 250° F. (121° C.) where the prior art oil resistant adhesive has begun to set up while the adhesive composition of the present invention is still somewhat fluid. As will be discussed below, the Applicants believe that the improved visco-thermal properties of the adhesives of the present invention overcome many of the material and process friendliness issues of prior art oil resistant adhesives while not becoming susceptible to undesirable permeation or bleedthrough.

Figure 8:
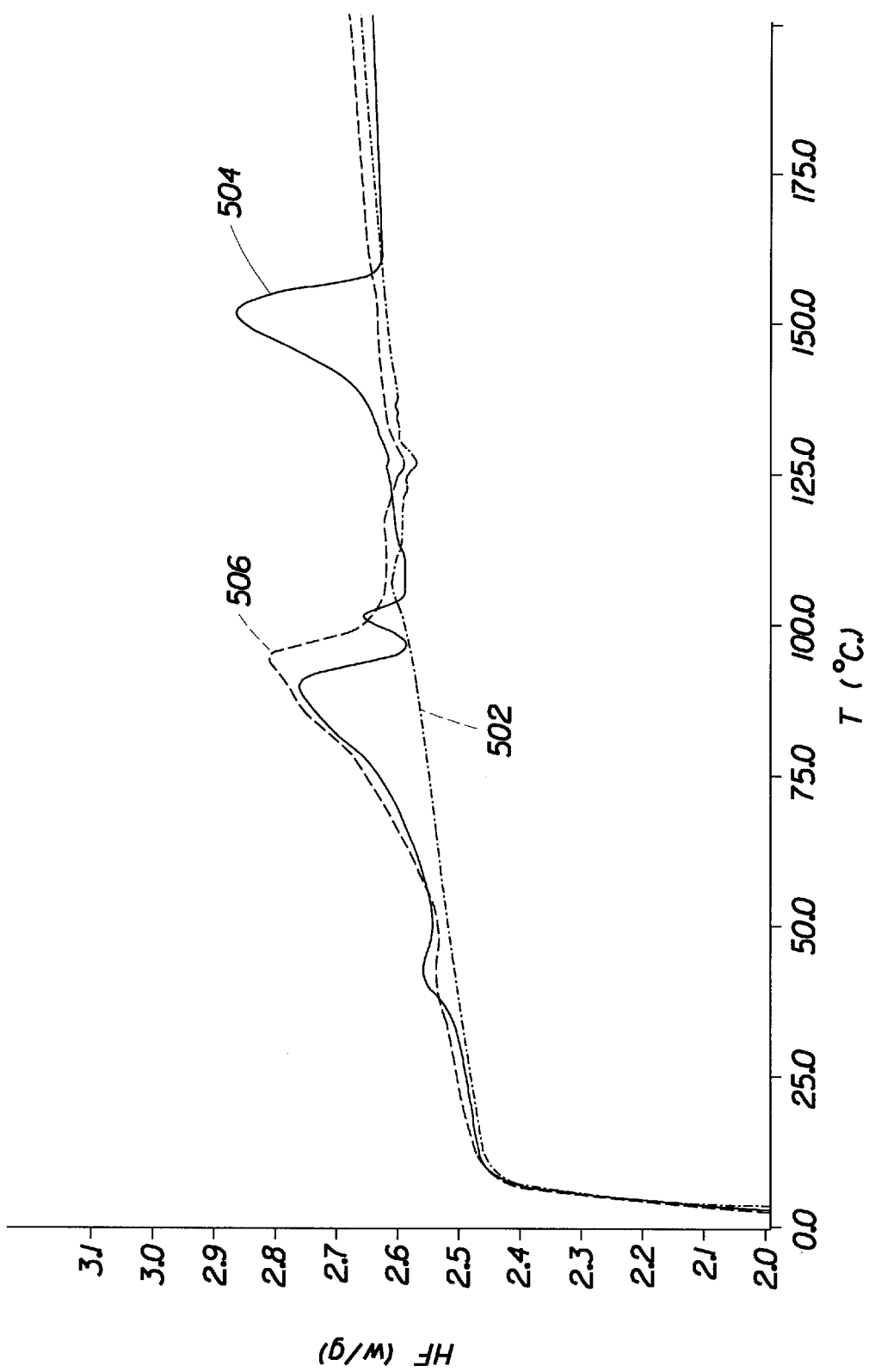
FIG. 8 is a graph of heat flow vs. Temperature for various adhesive compositions.

In particular, the Applicants believe that the lower heat of melting of the adhesives of the present invention means that set up time can be acceptably short while, at the same time, maintaining the desirable viscosity/temperature relationship described above. As is known, time is required for a fluid to flow over a certain distance for a given pressure differential and higher viscosity fluids require more flow time than lower viscosity fluids. As is also known heat transfer from a material depends on the temperature difference between the material and the surrounding environment, the area of the material exposed to the environment, the heat capacity of the material, and heat from any crystalline melting of the material. As can be seen in FIG. 8 (Example 5), the prior art oil resistant adhesive has a crystalline melting region at about 300° F. (150° C.). As heat is removed the prior art adhesive begins to increase in viscosity as a portion of the adhesive crystallizes. While the adhesive of the present invention does not show this crystalline melting region, the Applicants believe that the combination of the lower application temperature of the adhesives of the present invention (see Example 4) and the relatively low heat transfer coefficient (related to the slope of the baseline of the curves of FIG. 8) means that an adhesive of the present invention cools sufficiently rapidly to have an acceptably short set up time.

One aspect of this desirable viscosity temperature relationship is clearly demonstrated in Example 5. In this example, melt time for adhesives of the present invention is compared to adhesives of the prior art. One of the prior art adhesives (H2511) is widely used in the assembly of absorbent articles but has unacceptable oil resistance. The other adhesive (H9254) is representative of the oil resistant adhesives of the prior art. As can be clearly seen from the data in FIG. 7, an adhesive according to the present invention (H9268) has both a melting profile much closer to that of current adhesives that are widely used while also having desirable oil resistance.

The Applicants believe the differences in melting profile can be explained by the heat of fusion of the various adhesive compositions. As used herein the term "heat of fusion" is the amount of energy required for crystalline melting of a material. Heat of fusion can be measured using differential scanning calorimetry techniques as are described in the TEST METHODS section below. In order to be suitable for use as an adhesive of the present invention, the heat of fusion of an adhesive composition should be less than about 20 joules per gram. Preferably, the heat of fusion is less than about 15 joules per gram. Surprisingly, the Applicants have found that, by providing such a reduction in heat of fusion compared to adhesive compositions of the prior art, the adhesives of the present invention melt much more rapidly. Also, a low heat of fusion and the resulting lower application temperature allows the adhesive compositions of the present invention to cool and increase in viscosity quickly enough to substantially reduce the risk of process hygiene issues and other issues related to undesirable flow of the adhesive after application thereof.

D. Cuff Assembly and Attachment

As noted above oil resistant adhesive materials are suitable for use as any or all of a flap attachment member 88, an elastic attachment member 90, a proximal securement member 92, or a spacing elastic attachment member 94. The following discusses one means of applying an adhesive of the present invention for use as a spacing elastic attachment member 94 for forming a barrier cuff 62. One of skill in the art will recognize analogous methods for using the adhesive materials of the present invention for other of the elements of the diaper 20.

As can be seen most clearly in FIG. 3, the spacing elastic member 76 is enclosed in a tunnel that is formed when an end of the barrier cuff member 63 is folded back upon itself, the spacing elastic member 76 being secured in the tunnel by spacing elastic attachment members 94. The distal edge 66 of the barrier cuff is spaced away from the body surface 40 by the elastic gathering action of the spacing elastic member 76. To: 1) form this tunnel, 2) attach the spacing elastic member 76, and 3) provide the gathering action, the following steps have been found to be suitable.

First, a spacing elastic member 76 is provided. Any elastically contractible material is suitable for use as the spacing elastic member 76. Particular materials are also described in the aforementioned U.S. Pat. No. 4,695,278.

Second, a suitable spacing elastic attachment member 94 is provided. As noted above, the adhesive compositions of the present invention are particularly preferred.

Third, the spacing elastic member 76 and the spacing elastic attachment member 94 are associated using means known to the art. Suitable means include, but are not limited to, slot extrusion of the spacing elastic attachment member 94 onto the spacing elastic 76 and spraying the spacing elastic attachment member 94 onto the spacing elastic 76. Particularly preferred is spraying the spacing elastic attachment member 94 onto the spacing elastic 76 using a spiral pattern as is known to the art whereby the width of the spirals are such that the spacing elastic attachment member 94 is carried around the spacing elastic member 76 so as to contact all the surfaces thereof. That is, the spacing elastic member 76 is wrapped by the spacing elastic attachment member 94.

Fourth, a web of material suitable for forming the barrier cuff member 63 is provided. Such materials are described as being suitable for forming the barrier cuff 62 in the aforementioned U.S. Pat. No. 4,695,278.

Fifth, the wrapped spacing elastic attachment member 76 is joined to the barrier cuff member 63 (forming the barrier cuff 62) by folding a portion of the barrier cuff member 63 about the wrapped spacing elastic member 76 and combining the barrier cuff member 63 and the wrapped spacing elastic member 76 using means known to the art. The longitudinal edge of the portion of the spacing elastic member can also be joined to the remainder of the spacing elastic member using barrier cuff closure means 96, such as a combination of heat and pressure, commonly known as crimping, adhesive means or other means as may be known to the art.

E. Application of Skin Care Composition To Cuffs (Or Other Webs)

In preparing treated cuff products according to the present invention, the skin care composition is preferably applied to the body surface (i.e., wearer-contacting surface) of the cuff. However, since certain skin care compositions disclosed herein can penetrate or migrate through some of the cuff materials disclosed herein, the skin care composition may alternatively be applied to the garment surface of the cuff such that an effective amount of the skin care composition is disposed on the body surface. In fact, in some circumstances, this may be a preferred approach to achieve the benefits of a fully treated cuff (i.e., both sides are treated) though application is to one surface only.

Any of a variety of application methods that distribute lubricious materials having a molten or liquid consistency can be used to apply the skin care composition to the cuffs. Suitable application methods include coating (e.g., gravure or slot coating), spraying, printing (e.g., flexographic printing), extruding, or combinations of these or other application techniques (e.g. spraying the skin care composition on a rotating surface, such as a calendar roll, that then transfers via contact coating the skin care composition to the body surface of the diaper cuffs). If desired, the skin care composition can also be applied to both sides of the cuffs.

The manner of applying the skin care composition to the cuffs should be such that the cuffs do not become over saturated with the skin care composition. If the cuffs are treated with excessive amounts of the skin care composition, there is a greater potential for the skin care composition to migrate to undesired locations of the article, for example, into the interior of the article where it can have a detrimental effect on the absorbency of the underlying absorbent core. Also, saturation of the cuffs is not required to obtain the therapeutic and/or protective skin care composition benefits.

The minimum level of skin care composition to be applied to the cuff is the smallest amount effective in reducing erythema, diaper rash, red marking, skin irritation or other adverse skin conditions. (The compositions can also be effective in reducing the adherence of BM to the skin of the wearer.) Of course, the effective amount of a skin care composition will depend, to a large extent, on the particular skin care composition used. Because the emollient is substantially immobilized on the body surface of the cuff, less skin care composition is needed to impart the desired skin care benefits. Such relatively low levels of skin care composition are adequate to impart the desired therapeutic and/or protective skin care composition benefits to the cuff.

The skin care composition may be applied evenly and uniformly onto either or both surfaces of the cuff or portions thereof The skin care composition may also be applied in a pattern (i.e., stripes, boxes, dots, spirals, etc.). Preferably, the skin care composition is registered with the region of the cuff that will, in use, be most in contact with the wearer. Most preferably, as described in the Examples hereinafter, the skin care composition is applied in a stripe to a discrete portion of the cuff, e.g., a 1.4 inch wide (diaper lateral direction, such that the distal edge of the cuff is covered) and 11.75 inch long (diaper longitudinal direction) patch generally disposed in the crotch portion of the body surface of the cuff.

The skin care composition can also be applied nonuniformly to either or both surfaces of the cuff. By "nonuniform", it is meant that the amount, pattern of distribution, etc., of the skin care composition can vary over the cuff surface. For example, some portions of the treated surface of the cuff can have greater or lesser amounts of skin care composition, including portions of the surface that do not have any skin care composition on it.

The skin care composition can be applied to the cuff or a web that forms a portion of the cuff at any point during assembly. For example, the skin care composition can be applied to the cuff of the finished product before it has been packaged. The skin care composition can also be applied to the cuff or the web before it is combined with the other raw materials to form a finished product, either at the converting site prior to combination with other article components or as a pretreated stock material.

The skin care composition is typically applied from a melt thereof to the cuff. Since the skin care composition melts at significantly above ambient temperatures, it is usually applied as a heated coating to the cuff. Typically, the skin care composition is heated to a temperature in the range from about 35° to about 100° C., preferably from 40° to about 90° C., prior to being applied to the cuff. Once the melted skin care composition has been applied to the cuff, it is allowed to cool and solidify to form a solidified coating or film disposed on the surface of the cuff. Preferably, the application process is designed to aid in the cooling/set up of the composition.

Figure 5:
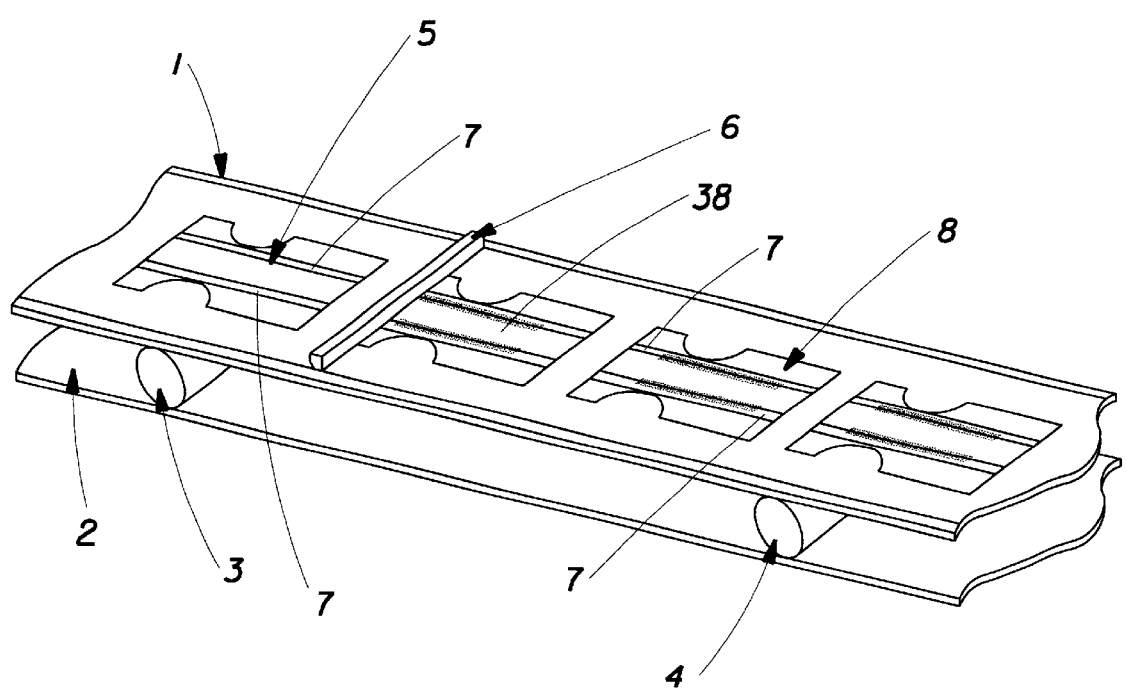
FIG. 5 is a schematic representation illustrating a preferred process for applying the composition of the present invention to diaper barrier cuffs.

In applying skin care compositions of the present invention to cuffs, slot coating, extrusion coating, gravure coating, and spraying methods are preferred. FIG. 5 illustrates a preferred method involving continuous or intermittent contact slot coating of the skin care composition on to a diaper barrier cuff during the converting operation. Referring to FIG. 5, conveyor belt 1 advances in the direction shown by the arrows on turning rolls 3 and 4 and becomes returning conveyor belt 2. Conveyor belt 1 carries nonlotioned diaper 5 to contact slot coating station 6 where the barrier cuff member 7 is coated with a hot, molten (e.g., 65° C.) skin care composition. After leaving slot coating station 6, the diaper 5 becomes diaper 8 having treated barrier cuffs. The amount of skin care composition transferred to barrier cuff member 7 is controlled by: (1) the rate at which the molten skin care composition is applied from contact slot coating station 6; and/or (2) the speed at which conveyor belt 1 travels under slot coating station 6; and/or (3) positioning of the contact slot coating station. (If desired, the coating station may be positioned so as to coat the barrier cuff member 7 as well as portions of the topsheet 38 such that both the cuff and the topsheet have a skin care composition disposed thereon.)

SPECIFIC ILLUSTRATIONS OF THE PREPARATION OF TREATED DIAPER CUFFS AND TOPSHEETS ACCORDING TO THE PRESENT INVENTION

The following are specific illustrations of treating cuffs and/or topsheets or webs with skin care compositions in accordance with the present invention:

EXAMPLE 1

This example is intended to demonstrate preparation of a diaper having cuffs assembled using an oil resistant adhesive of the present invention and treatment of the cuffs with a skin care composition.

A. Preparation of Skin Care Composition

A skin care composition (Composition A) is made by mixing the following melted (i.e., liquid) components together: Petrolatum (available from Witco Corp., Greenwich, Conn. as Perfecta®) Stearyl Alcohol (available from The Procter & Gamble Company, Cincinnati, Ohio as CO1897) and aloe extract (available from Madis Botanicals, Inc., South Hackensack, N.J. as Veragel Lipoid in Kaydol). The weight percentages of these components are shown in Table 2 below:

TABLE 2

| Component | Weight % |
| --- | --- |
| Petrolatum | 58 |
| Stearyl Alcohol | 41 |
| Aloe | 1 |

B. Preparation of Treated Diaper Leg Cuff by Hot Melt Coating

To assemble the cuffs, the spacing elastic members are operatively joined to the barrier cuff member by an adhesive according to the present invention, such as Findley H9268 (i.e. by applying the adhesive to the elastic member, folding the barrier cuff member about the adhesive treated elastic member, and combining the assembly) as discussed previously herein. The cuff is then joined to the topsheet using means known to the art to complete the assembly.

The assembly is then treated with skin care composition A. The composition is placed into a heated tank operating at a temperature of 170° F., for melting. The melted composition is subsequently applied with a contact applicator (e.g., a Meltex EP45 hot melt adhesive applicator head operating at a temperature of 170° F.) directly onto the body surface of the barrier cuffs of a diaper in a 1.4 inch wide (diaper lateral direction, such that the distal edge of the barrier cuff is covered) and 11.75 inch long (diaper longitudinal direction) area, the patch centered in the chassis in the longitudinal direction such that one or both ends of each spacing elastic member is covered by the skin care composition. Add-on level=0.0116 g/in$^2$ (18.0 g/m$^2$). These treated diapers are identified as Diaper 1 in Example 3.

EXAMPLE 2

This example is intended to describe preparation of a diaper having cuffs assembled using prior art adhesives and treatment of the cuffs with a skin care composition.

One set of diapers is provided with cuffs assembled using a prior art non oil resistant adhesive (H2511 from Ato Findley) in substantially the same manner as described in Example 1. A second set of diapers is provided with cuffs assembled using a prior art oil resistant adhesive (H9254 from Ato Findley). A portion of the first set of diapers (non oil resistant adhesive) and all of the diapers from the second set (oil resistant adhesive) is subsequently treated with skin care composition A (prepared in accordance with the procedure in Example 1) by melting the composition and applying the melted composition onto the body surface of the barrier cuffs of a diaper in a 1.4 inch wide (diaper lateral direction, such that the distal edge of the barrier cuff is covered) stripe on of each barrier cuff and extending the entire length of the barrier cuff in substantially the same manner as described in Example 1. Add-on level is about 0.0116 g/in$^2$ (18 g/m$^2$) for both sets of diapers. Products from this example are identified as follows: Diaper 2-non oil resistant adhesive, no treatment with skin care composition; Diaper 3-non oil resistant adhesive, treated with Composition A; and Diaper 4-prior art, oil resistant adhesive, treated with Composition A

EXAMPLE 3

This example is intended to demonstrate the oil resistance of adhesives of the present invention and of certain adhesives of the prior art when compared to typical adhesives of the prior art.

Cuffs from the diapers prepared according to Examples 1 and 2 are removed from the diapers and evaluated for creep according to the method described in the TEST METHODS section. Table 3 shows the results of this evaluation.

TABLE 3

| | | | Creep Evaluation | |
|---|---|---|---|---|
| Sample | Treated | Adhesive | (inches/mm) | (% > 0.35 in/8.9 mm) |
| Diaper 1* | Yes | H9268 | 0.09/2.3 | 4.7 |
| Diaper 2** | No | H2511 | 0.10/2.5 | 0.0 |
| Diaper 3** | Yes | H2511 | 0.27/6.9 | 17.8 |
| Diaper 4** | Yes | H9254 | 0.13/2.8 | 4.6 |

*Cuffs assembled using adhesive of the present invention (H9268)
**Cuffs assembled using adhesives of the prior art (H2511 and H9254)

As can be seen, treated cuffs assembled using either of the oil resistant adhesives have creep values that are comparable to the creep value of the untreated, non oil resistant prior art adhesive. As can also be seen, treatment of cuffs that are assembled using a non oil resistant adhesive results in a substantial increase in creep.

EXAMPLE 4

This example is intended to demonstrate the material friendliness of adhesives of the present invention.

Two prior art adhesives (H2511 and X9254) and the adhesive of the present invention (H9268) are used as an elastic attachment member for securing a flap elastic member as part of a diaper assembly test. The elastic attachment member joins the flap elastic member to the backsheet and to the topsheet. The backsheet is a laminate of a carded nonwoven and a porous film as is available from Fibertech of Simpsonville, S.C. as product 1008. All adhesive materials are applied at substantially the same basis weight in a pattern of spirals as is known to the art. The finished diapers are then evaluated for backsheet integrity in the vicinity of the elastic attachment member. The results of this evaluation are given in Table 4.

TABLE 4

| Adhesive Type | Application Temperature | Backsheet Integrity |
|---|---|---|
| H2511* | 325° F./162° C. | No substantial deformation |
| H9254* | 375° F./191° C. | Visible deformation, holes, weakening |
| H9268** | 350° F./177° C. | Visible deformation |

*Adhesive of the prior art
**Adhesive of the present invention.

As can be seen, at an application temperature of about 375° F./191°, holes and weakening of the backsheet begin to appear for the polyethylene film topsheet.

EXAMPLE 5

This example is intended to demonstrate one aspect of the process friendliness of adhesives of the present invention.

Figure 7:
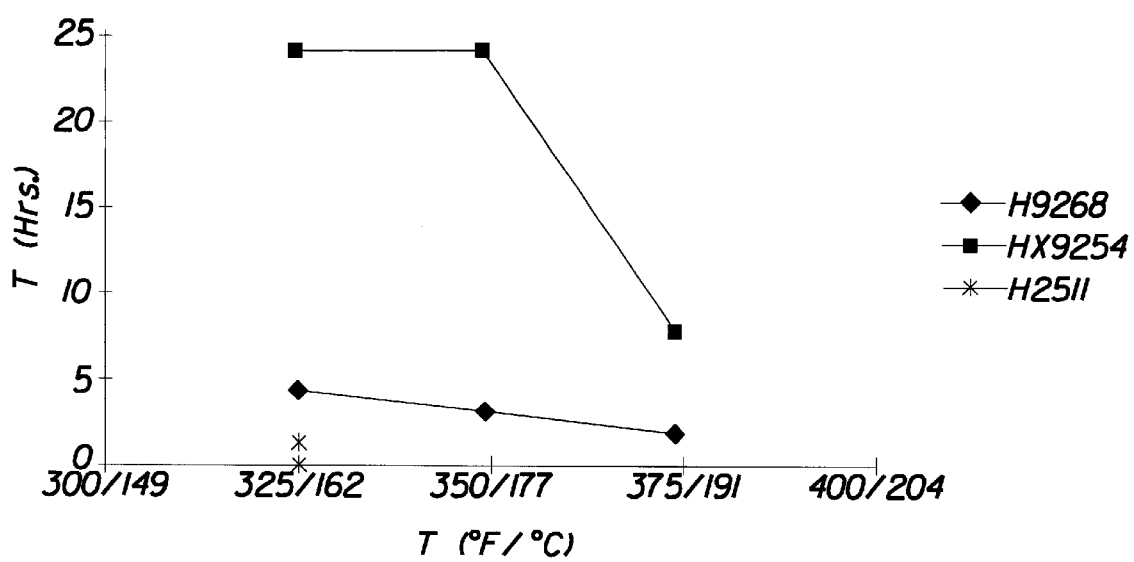
FIG. 7 is a graph comparing melt time with melt temperature for various adhesive compositions.

The example compares the melting behavior of two prior art adhesives:

H2511, which is available from Ato Findley, Inc. of Battle Creek, Mo., is widely used in the assembly of absorbent articles but has unacceptable oil resistance; and H9254, also available from Ato Findley, is representative of the oil resistant adhesives of the prior art;

with an oil resistant adhesive (H9268, also available from Ato Findley) of the present invention in two ways:

1) The time (t) in hours required to completely melt 30 pounds (13.6 kg) of each of the adhesives at various temperatures (T) was determined. The results are shown in FIG. 7. As can be clearly seen, the adhesive of the present invention and the widely used prior art adhesive having unsatisfactory oil resistance have a much more similar melt profile than the prior art oil resistant adhesive.

2) The heat of fusion for each of the adhesives was measured according to the Differential Scanning Calorimetry Method described in the TEST METHODS section below. The results of these measurements are shown in Table 5.

TABLE 5

| Adhesive Type | Heat of Fusion (Joules/gram) |
| --- | --- |
| H2511* | 2.64 |
| H9254* | 27.10 |
| H9268** | 13.09 |

*Adhesive of the prior art
**Adhesive of the present invention.

FIG. 8 shows the results of this experiment in an alternative manner where the heat flow (HF) in watts per gram is plotted against temperature (T). Curves are presented for a prior art, non-oil resistant adhesive composition (H2511, shown as 502 in FIG. 8), a prior art, oil resistant adhesive composition (H9254, shown as 504), and an adhesive composition of the present invention (H9268, shown as 506). As is known, the area under the portions of various peaks that lies above the baseline heating curve may be summed to determine the heat of fusion. As is clearly shown in FIG. 8, the prior art, oil resistant adhesive contains a peak at a temperature of about 300° F. (150° C.). This means, unless such prior art adhesives are heated above this temperature, they will not melt.

TEST METHODS

Elastic Creep

Overview

Displacement of the ends of cuff elastic members is determined after cuffs are stored under tension (~100% elongation) for 2 hours at 100° F.

Apparatus

Incubator Capable of maintaining temperature of 100±1° F. A suitable incubator is available from VWR Scientific of West Chester, Pa. as a Model 2020.

Sample Substrate Annular cylinder having an eight inch (20 cm) inner diameter and a 0.375 inch (9.5 mm) wall thickness. A suitable substrate is a paperboard core with the above dimensions as is used for winding web substrates. Such cores are available from Sonoco of Hartsville, S.C.

Sample Preparation

1) Carefully, break and/or cut out all the tackdown bonds and separate the cuff from the diaper.
2) Before the cuff is removed, mark EACH strand of elastic on both ends at the point where it begins to pucker (gathers/no gathers). (Note: If it is difficult to determine where the gathers begin, remove the cuff and place onto a light board just to mark the elastic pucker). If the elastic glued length runs into the tackdown bonds, mark the footprint at the longest tackdown bond. Each cuff will have a pair of marks for each elastic member.

Operation

1) Attach the sample strip to the substrate so it is under tension. The following method has been found suitable.
   a) Place a sample strip on the sample substrate with the garment surface up and attach one end of the sample strip to the substrate being sure to allow full freedom of movement for the unglued ends of the elastic members. For the paperboard sample substrates discussed above, sample strips may be attached by stapling them to the substrate.
   b) Stretch the sample strip to remove all gathers (~100% elongation). The stretched length is typically the same as the distance between the end margins of the diaper from which the sample cuff was removed.
   c) While maintaining tension, attach the free end of the sample strip to the substrate as in step a.
2) Place the stretched assembly into the incubator (incubator set point 100° F.) being careful to minimize the amount of time the incubator is open (It takes the incubator five to ten minutes to recover if the door is left open 30 seconds and this will have a significant effect on the test results). Record the time the assembly was placed in the incubator.
3) Remove the assembly after two hours of incubation. Record the time the assembly was removed from the incubator. Allow the sample to reequilibrate to room temperature before making any measurements (~5 minutes).

Measurement and Calculations

1) For each elastic end, determine if the end has moved relative to the initial mark. Measure and record any movement to the nearest 0.1 inch (2 mm). For no movement record 0.
2) For each end calculate the time (minutes) in the incubator by determining the elapsed time based on the placement and removal times.
3) Sum the total inches (millimeters) of creep for each cuff sample. For example, a cuff having three elastic members will have six elastic ends in the sum.
4) For each cuff sample calculate the average creep per elastic end according to the following equation:

$$\text{Inches of Creep/Elastic End/Hour} = \frac{\text{Total Inches Creep in Two Hours}}{\text{Number of Elastic Ends}} * \frac{\text{Elasped Time}}{120}$$

5) Repeat steps 1–4 for at least 25 cuffs per condition.
6) Report the average Inches of Creep/Elastic End

Differential Scanning Calorimetry

The method described in ASTM Standard Method D3417-83 is suitable. The following clarifications are provided for additional detail.

1) A suitable differential scanning calorimeter apparatus is available from Perkin Elmer of Norwalk, Conn. as Model DSC-7. This instrument provides for automated calculation of curve areas rather than the planimeter method described in Section 11 of the standard method.
2) Intermediate samples may be removed from bulk adhesive blocks using a heated knife (available from Seal, Inc. of Derby, Conn. as a Selector Custom Iron) prior to cutting final samples as described in Section 8 of the standard method.
3) All instrument calibrations are run at a heating rate of 10° C./minute rather than 20° C./minute (Section 9 of the standard method recommends using the same heating rate for calibration and sample evaluation).
4) All samples are provided with an identical imposed thermal history by following the following regimen:
   a) Heat each sample from 0° C. to 200° C. at a rate of 20° C./minute.
   b) Cool each sample from 200° C. to 0° C. at a rate of 20° C./minute.
   c) Heat each sample from 0° C. to 200° C. at a rate of 20° C./minute.

Heat of fusion measurements are made on the second heating.

What is claimed is:

1. An absorbent article to be worn by a wearer adjacent the wearer's skin, the absorbent article comprising:
    a chassis comprising:
        an outer covering layer comprising:
            a backsheet; and
            a liquid pervious topsheet joined to said backsheet; and
        an absorbent core positioned between said topsheet and said backsheet;
    a cuff joined to said chassis, said cuff having a first surface and a second surface disposed opposite said first surface, said cuff comprising a cuff member and an elastic member wherein said elastic member has opposed elastic ends and is joined to said cuff member using an oil resistant adhesive, wherein said adhesive:
        has an apparent viscosity less than about 8000 centipoise at a temperature of 177° C. and less than about 50,000 centipoise at a temperature of 121° C. and a heat of fusion less than about 20 joules per gram; and
    less than about 10 percent of said elastic ends exhibit a creep value greater than about 0.35 inches (8.9 mm) when said cuff is evaluated according to an elastic creep method; and
    an effective amount of a skin care composition disposed on said cuff, said skin care composition being semi-solid or solid at 20° C. and at least partially transferable to a wearer's skin by contact, normal wearer motion and/or body heat.

2. The absorbent article of claim 1 wherein a quantity of said skin care composition is disposed on said cuff whereby said quantity of said skin care composition disposed on said cuff ranges from about 0.05 mg/in$^2$ to about 80 mg/in$^2$.

3. The absorbent article of claim 1 wherein said skin care composition comprises:
    (i) from about 10% to about 95% of an emollient having a plastic or fluid consistency at 20° C.; and
    (ii) from about 5% to about 90% of an agent capable of immobilizing said emollient on said cuff.

4. The absorbent article of claim 3 wherein said emollient comprises a component selected from the group consisting of petroleum-based emollients, fatty acid ester emollients, polysiloxane emollients, sucrose ester fatty acids, alkyl ethoxylates emollients and mixtures thereof.

5. The absorbent article of claim 4 wherein said agent capable of immobilizing said emollient on said cuff is selected from the group consisting of polyhydroxy fatty acid esters, polyhydroxy fatty acid amides, $C_{14}$–$C_{22}$ fatty alcohols, $C_{12}$–$C_{22}$ fatty acids, $C_{12}$–$C_{22}$ fatty alcohol ethoxylates, and mixtures thereof.

6. The absorbent article of claim 5 wherein said emollient contains about 5% or less water and comprises a petroleum based emollient selected from the group consisting of mineral oil, petrolatum, and mixtures thereof.

7. The absorbent article of claim 1 wherein said skin care composition is disposed on said first surface.

8. The absorbent article of claim 7 wherein said first surface comprises the surface facing away from the wearer during use so as to form a garment surface.

9. The absorbent article of claim 8 wherein said skin care composition is capable of being transferred.

10. The absorbent article of claim 1 wherein said cuff comprises a gasketing cuff comprising a side flap formed from a portion of said topsheet.

11. The absorbent article of claim 1 wherein said cuff comprises a barrier cuff that is formed unitarily with said topsheet.

12. An absorbent article to be worn by a wearer adjacent the wearer's skin, the absorbent article comprising:
    a chassis having edges, said chassis comprising:
        an outer covering layer; and
        an absorbent core encased in said outer covering layer;
    a barrier cuff joined to said chassis, said barrier cuff comprising a separate barrier cuff member having a proximal edge and a distal edge in spaced relation to said proximal edge, said proximal edge being joined to said outer covering layer, a portion of said distal edge not being secured to the absorbent article, and a spacing elastic member operatively associated with said distal edge for allowing said barrier cuff to stand upwardly away from said outer covering layer wherein said elastic member has opposed elastic ends and is joined to said cuff member using an oil resistant adhesive, wherein said adhesive:
        has an apparent viscosity less than about 8000 centipoise at a temperature of 177° C. and less than about 50,000 centipoise at a temperature of 121° C. and a heat of fusion less than about 20 joules per gram and
    less than about 10 percent of said elastic ends exhibit a creep value greater than about 0.35 inches (8.9 mm) when said cuff is evaluated according to an elastic creep method; and
    an effective amount of a skin care composition disposed on said barrier cuff member, said skin care composition being semi-solid or solid at 20° C. and at least partially transferable to a wearer's skin.

13. The absorbent article of claim 12 additionally comprising a gasketing cuff positioned adjacent said barrier cuff.

14. The absorbent article of claim 12 wherein the absorbent article is a diaper.

15. The absorbent article of claim 12 wherein the absorbent article is a sanitary napkin.

* * * * *

UNITED STATES PATENT AND TRADEMARK OFFICE
CERTIFICATE OF CORRECTION

PATENT NO.    : 6,270,487 B1
DATED         : August 7, 2001
INVENTOR(S)   : Astrid Annette Sheehan et al.

It is certified that error appears in the above-identified patent and that said Letters Patent is hereby corrected as shown below:

Title page,
FOREIGN PATENT DOCUMENTS, delete "WO 96/38739" and insert -- WO 97/38739 --.
ABSTRACT, 4th line, delete "wearers" and insert -- wearer's --.

Column 5,
Line 17, delete "wearers" and insert -- wearer's --.

Column 8,
Line 28, delete "cuffs" and insert -- cuff's --.

Column 10,
Line 13, delete "08/926,926,553" and insert -- 08/926,533 --.

Column 12,
Line 60, delete second "No.".
Line 64, delete second "No.".

Column 14,
Line 51, delete second "No.".

Column 18,
Line 3, delete "cuffs" and insert -- cuff's --.

Column 19,
Line 36, delete "6" and insert -- 16 --.

Column 31,
Line 30, insert -- . -- "thereof".

UNITED STATES PATENT AND TRADEMARK OFFICE
CERTIFICATE OF CORRECTION

PATENT NO. : 6,270,487 B1
DATED : August 7, 2001
INVENTOR(S) : Astrid Annette Sheehan et al.

It is certified that error appears in the above-identified patent and that said Letters Patent is hereby corrected as shown below:

<u>Column 34,</u>
Line 47, delete "Mo." and insert -- Mi. --.

Signed and Sealed this

Seventh Day of May, 2002

Attest:

Attesting Officer

JAMES E. ROGAN
*Director of the United States Patent and Trademark Office*